(12) United States Patent
Buckland et al.

(10) Patent No.: US 10,271,725 B2
(45) Date of Patent: Apr. 30, 2019

(54) HYBRID TELESCOPE FOR OPTICAL BEAM DELIVERY AND RELATED SYSTEMS

(71) Applicant: Bioptigen, Inc., Morrisville, NC (US)

(72) Inventors: Eric L. Buckland, Hickory, NC (US); Andrew Murnan, Saratoga Springs, NY (US); Nestor O. Farmiga, Rochester, NY (US); Robert H. Hart, Cary, NC (US); Christopher Saxer, Chapel Hill, NC (US)

(73) Assignee: Bioptigen, Inc., Morrisville, NC (US)

( * ) Notice: Subject to any disclaimer, the term of this patent is extended or adjusted under 35 U.S.C. 154(b) by 22 days.

(21) Appl. No.: 15/826,966

(22) Filed: Nov. 30, 2017

(65) Prior Publication Data

US 2018/0084993 A1 Mar. 29, 2018

Related U.S. Application Data

(62) Division of application No. 14/295,664, filed on Jun. 4, 2014, now Pat. No. 9,949,634.

(Continued)

(51) Int. Cl.
*A61B 3/10* (2006.01)
*G01B 9/02* (2006.01)
(Continued)

(52) U.S. Cl.
CPC ............ *A61B 3/102* (2013.01); *A61B 3/1025* (2013.01); *G01B 9/02038* (2013.01);
(Continued)

(58) Field of Classification Search
CPC .. A61B 3/102; A61B 3/1025; G01B 9/02091; G01B 9/02042; G01B 9/02038; G02B 19/0014
See application file for complete search history.

(56) References Cited

U.S. PATENT DOCUMENTS 4,167,302 A 9/1979 Karasawa
4,431,258 A 2/1984 Fye
(Continued)

FOREIGN PATENT DOCUMENTS

CN 101382644 A 3/2009
CN 102596125 A 7/2012
(Continued)

OTHER PUBLICATIONS

Brandenburg R. et al., "Real-time in vivo imaging of dental tissue by means of optical coherence tomography (OCT)", *Optics Communications*, 227 (2003), 203-211.
(Continued)

*Primary Examiner* — Jack Dinh
(74) *Attorney, Agent, or Firm* — Stanek Lemon Crouse & Meeks, PA

(57) ABSTRACT

Optical coherence tomography (OCT) imaging systems are provided including a source of broadband optical radiation coupled to a sample arm of the OCT imaging system; a beam shaping optical assembly in the sample arm, the beam shaping optical assembly being configured to receive optical radiation from the source as a beam of optical radiation and to shape the spatial profile of the beam of optical radiation; a scan mirror assembly coupled to the beam shaping optical assembly; and objective lens assembly coupled to the beam shaping optical assembly. The beam shaping optical assembly includes a lens assembly configured to change a NA of the OCT system without changing a focus; to change a focus of the OCT system without changing a NA of the system; or to change both the NA and the focus of the OCT system responsive to a control input.

12 Claims, 21 Drawing Sheets

Related U.S. Application Data

(60) Provisional application No. 61/830,820, filed on Jun. 4, 2013.

(51) Int. Cl.
   *G02B 19/00* (2006.01)
   *G02B 23/24* (2006.01)

(52) U.S. Cl.
   CPC ..... *G01B 9/02042* (2013.01); *G01B 9/02091* (2013.01); *G02B 19/0014* (2013.01); *G02B 23/2407* (2013.01)

(56) References Cited

U.S. PATENT DOCUMENTS

| | | | |
|---|---|---|---|
| 4,544,243 | A | 10/1985 | Munnerlyn |
| 4,561,080 | A | 12/1985 | Yamazaki |
| 4,930,868 | A | 6/1990 | Gerlitz |
| 5,055,663 | A | 10/1991 | Morimoto et al. |
| 5,061,018 | A | 10/1991 | Pederson et al. |
| 5,103,439 | A | 4/1992 | Bierhoff et al. |
| 5,168,386 | A | 12/1992 | Galbraith |
| 5,220,450 | A | 6/1993 | Iizuka |
| 5,491,524 | A | 2/1996 | Hellmuth et al. |
| 5,493,109 | A | 2/1996 | Wei et al. |
| 5,795,295 | A | 8/1998 | Hellmuth et al. |
| 5,889,750 | A | 3/1999 | Summers et al. |
| 5,907,431 | A | 5/1999 | Stuttler |
| 6,004,314 | A | 12/1999 | Wei et al. |
| 6,333,781 | B1 | 12/2001 | Shigematsu |
| 6,419,360 | B1 | 7/2002 | Hauger et al. |
| 6,426,840 | B1 | 7/2002 | Partanen et al. |
| 6,451,010 | B1 | 9/2002 | Angeley |
| 6,678,090 | B2 | 1/2004 | Spink |
| 6,763,259 | B1 | 7/2004 | Hauger et al. |
| 6,943,942 | B2 | 9/2005 | Horiguchi et al. |
| 7,072,047 | B2 | 7/2006 | Westphal et al. |
| 7,145,727 | B2 | 12/2006 | Hsieh |
| 7,246,905 | B2 | 7/2007 | Benedikt et al. |
| 7,387,385 | B2 | 6/2008 | Sander |
| 7,408,705 | B2 | 8/2008 | Horiguchi et al. |
| 7,481,536 | B2 | 1/2009 | Wong et al. |
| 7,669,262 | B2 | 3/2010 | Skripps et al. |
| 7,699,468 | B2 | 4/2010 | Gaida |
| 7,719,692 | B2 | 5/2010 | Izatt et al. |
| 7,733,497 | B2 | 6/2010 | Yun et al. |
| 7,742,174 | B2 | 6/2010 | Izatt et al. |
| 7,791,794 | B2 | 9/2010 | Reimer et al. |
| 7,839,494 | B2 | 11/2010 | Reimer et al. |
| 7,889,423 | B2 | 2/2011 | Reimer et al. |
| 7,901,080 | B2 | 3/2011 | Hauger et al. |
| 8,023,120 | B2 | 9/2011 | Reimer et al. |
| 8,049,873 | B2 | 11/2011 | Hauger et al. |
| 8,189,192 | B2 | 5/2012 | Huenina et al. |
| 8,310,674 | B2 | 11/2012 | Huening et al. |
| 8,348,427 | B2 | 1/2013 | Buckland et al. |
| 8,401,257 | B2 | 3/2013 | Izatt et al. |
| 8,425,037 | B2 | 4/2013 | Uhlhorn et al. |
| 8,625,104 | B2 | 1/2014 | Izatt et al. |
| 8,693,745 | B2 | 4/2014 | Izatt et al. |
| 8,777,412 | B2 | 7/2014 | Buckland et al. |
| 8,797,530 | B2 | 8/2014 | Saxer et al. |
| 8,864,309 | B2 | 10/2014 | Buckland |
| 2002/0173778 | A1 | 11/2002 | Knopp et al. |
| 2003/0139736 | A1 | 7/2003 | Sander |
| 2003/0218755 | A1 | 11/2003 | Wei et al. |
| 2004/0036838 | A1 | 2/2004 | Podoleanu et al. |
| 2004/0109231 | A1 | 6/2004 | Haisch et al. |
| 2005/0068881 | A1 | 3/2005 | Kimura et al. |
| 2005/0277913 | A1 | 12/2005 | McCary |
| 2005/0283058 | A1 | 12/2005 | Choo-Smith et al. |
| 2006/0050408 | A1 | 3/2006 | Hakko et al. |
| 2006/0195074 | A1 | 8/2006 | Bartoli |
| 2007/0030446 | A1 | 2/2007 | Su et al. |
| 2007/0159595 | A1 | 7/2007 | Fukuma et al. |
| 2007/0258095 | A1 | 11/2007 | Olivier et al. |
| 2007/0282313 | A1 | 12/2007 | Huang et al. |
| 2007/0291277 | A1 | 12/2007 | Everett et al. |
| 2008/0004610 | A1 | 1/2008 | Miller et al. |
| 2008/0117504 | A1 | 5/2008 | Reimer et al. |
| 2008/0133019 | A1 | 6/2008 | Andrysek |
| 2008/0198329 | A1 | 8/2008 | Gaida |
| 2008/0304144 | A1 | 12/2008 | Reimer et al. |
| 2009/0141240 | A1 | 6/2009 | Weitz et al. |
| 2009/0244485 | A1 | 10/2009 | Walsh et al. |
| 2009/0257065 | A1 | 10/2009 | Hauger et al. |
| 2010/0030056 | A1 | 2/2010 | Abramov |
| 2010/0309478 | A1 | 12/2010 | Reimer et al. |
| 2010/0321700 | A1 | 12/2010 | Hirose et al. |
| 2010/0324542 | A1 | 12/2010 | Kurtz |
| 2010/0324543 | A1 | 12/2010 | Kurtz |
| 2011/0001926 | A1 | 1/2011 | Mann et al. |
| 2011/0028948 | A1 | 2/2011 | Raksi et al. |
| 2011/0096291 | A1 | 4/2011 | Buckland et al. |
| 2011/0116044 | A1 | 5/2011 | Nozato et al. |
| 2011/0173778 | A1 | 7/2011 | Wales |
| 2011/0202046 | A1 | 8/2011 | Angeley et al. |
| 2011/0242483 | A1 | 10/2011 | Shea et al. |
| 2011/0299034 | A1 | 12/2011 | Walsh et al. |
| 2012/0022408 | A1 | 1/2012 | Hubschman |
| 2012/0026462 | A1 | 2/2012 | Uhlhorn et al. |
| 2012/0063660 | A1 | 3/2012 | Imamura et al. |
| 2012/0074294 | A1 | 3/2012 | Streuber et al. |
| 2012/0184846 | A1 | 7/2012 | Izatt et al. |
| 2012/0197102 | A1 | 8/2012 | Hanebuchi et al. |
| 2012/0215155 | A1 | 8/2012 | Muller et al. |
| 2012/0242988 | A1 | 9/2012 | Saxer et al. |
| 2012/0262720 | A1 | 10/2012 | Brown et al. |
| 2012/0293771 | A1 | 11/2012 | Nozato et al. |
| 2013/0003017 | A1 | 1/2013 | Muto |
| 2013/0141695 | A1 | 6/2013 | Buckland et al. |
| 2013/0158531 | A1 | 6/2013 | Goldshleger et al. |
| 2013/0165763 | A1 | 6/2013 | Huang et al. |
| 2013/0172861 | A1 | 7/2013 | Youssefi |
| 2013/0190737 | A1 | 7/2013 | Muller et al. |
| 2013/0265545 | A1 | 10/2013 | Buckland et al. |
| 2014/0194860 | A1 | 7/2014 | Dick et al. |

FOREIGN PATENT DOCUMENTS

| | | |
|---|---|---|
| CN | 102811684 A | 12/2012 |
| CN | 104334072 A | 2/2015 |
| EP | 0 697 611 A2 | 2/1996 |
| EP | 1 659 438 B1 | 3/2009 |
| EP | 2 322 083 A1 | 5/2011 |
| JP | 2010-279576 A | 12/2010 |
| JP | 2011-024842 A | 2/2011 |
| JP | 2011-104370 A | 6/2011 |
| JP | 2011-147612 A | 8/2011 |
| WO | WO 2008/034609 A1 | 3/2008 |
| WO | WO 2011/017019 A2 | 2/2011 |
| WO | WO 2011/091326 A1 | 7/2011 |
| WO | WO 2013/059719 A1 | 4/2013 |
| WO | WO 2013/151879 A1 | 10/2013 |

OTHER PUBLICATIONS

Davis A.M. et al., "In vivo spectral domain optical coherence tomography volumetric imaging and spectral Doppler velocimetry of early stage embryonic chicken heart development", *J. Opt. Soc. Am. A.*, vol. 25, No. 12, Dec. 2008, pp. 3134-3143.

Geerling G. et al., "Intraoperative 2-Dimensional Optical Coherence Tomography as a New Tool for Anterior Segment Surgery", *Arch Ophthalmol.* 2005;123:253-257.

Izatt J.A. et al., "Optical coherence microscopy in scattering media", *Optics Letters*, vol. 19, No. 8, Apr. 15, 1994, pp. 590-592.

Izatt S. D. et al., "In Vivo Imaging of the *Drosophila melanogaster* heart Using a Novel Optical Coherence Tomography Microscope", *Proc. of SPIE*, vol. 5701, pp. 122-127, Downloaded from SPIE Digital Library on May 16, 2011.

(56) References Cited

OTHER PUBLICATIONS

Maschio M.D. et al., "Three-dimensional in vivo scanning microscopy with inertia-free focus control", *Optics Letters*, Sep. 1, 2011, vol. 36, No. 17, pp. 3503-3505.
Murali, Supraja *"Design of a Dynamic Focusing Microscope Objective for OCT Imaging"*, MS Thesis, University of Central Florida, Orlando, Florida, 2005.
Notification of Transmittal of the International Search Report and the Written Opinion of the International Searching Authority, or the Declaration, PCT/US2013/034544, dated Jul. 3, 2013.
Notification of Transmittal of the International Search Report and the Written Opinion of the International Searching Authority, of the Declaration, PCT/US2012/067951, dated Mar. 5, 2013.
Qi B. et al., "Dynamic focus control in high-speed optical coherence tomography based on a microelectromechanical mirror", *Optics Communications*, 232 (2004), 123-128.
Radhakrishnan S. et al., "Real-Time Optical Coherence Tomography of the Anterior Segment at 1310 nm", *Arch Ophthalmol.*, 2001;119:1179-1185.
Tao Y.K. et al., "Intraoperative spectral domain optical coherence tomography for vitreoretinal surgery", *Optics Letters*, Oct. 15, 2010, vol. 35, No. 20, pp. 3315-3317.
Notification Concerning Transmittal of International Preliminary Report on Patentability, PCT/US2013/034544, dated Oct. 7, 2014, 8 pages.
Invitation to Pay Additional Fees and, Where Applicable, Protest Fees, PCT/US2014/048552, dated Oct. 31, 2014.
Notification of Transmittal of the International Search Report and the Written Opinion of the International Searching Authority, or the Declaration, PCT/US2014/048552, dated Feb. 2, 2015, 15 pages.
Notification of Transmittal of the International Search Report and the Written Opinion of the International Searching Authority, or the Declaration, PCT/US2014/040836, dated Feb. 4, 2015, 15 pages.
Notification Concerning Transmittal of International Preliminary Report on Patentability, PCT/US2014/040836, dated Dec. 8, 2015, 10 pages.
Notification Concerning Transmittal of International Preliminary Report on Patentability, PCT/US2014/048552, dated Feb. 11, 2016, 9 pages.
Dal Maschio et al. "Three-dimensional in vivo scanning microscopy with inertia-free focus control," Optics Letters, vol. 36, No. 17, Sep. 1, 2011, pp. 3503-3505.
First Office Action, Chinese Patent Application No. 201380029541.0, dated Feb. 22, 2016, 15 pages.
International Search Report and Written Opinion Corresponding to International Application No. PCT/US2014/053113; dated Dec. 2, 2014, 11 Pages.
Notification Concerning Transmittal of International Preliminary Report on Patentability, PCT/US2014/053113, dated Mar. 10, 2016.
Notification Concerning Transmittal of International Preliminary Report on Patentability, PCT/US2014/040836, dated Dec. 17, 2015.
Notification of Reasons for Refusal, JP Pat. Appl. No. 2016-518427, dated Jan. 23, 2017, 12 pages.
First Notification of Office Action, Chinese Patent Application No. 201480032285.5, dated Jan. 24, 2017, 14 pages.
Second Notification of Office Action, Chinese Patent Application No. 201480032285.5, dated Jul. 25, 2017, 15 pages.
Decision of Refusal, JP Application No. 2016-525842, dated Jan. 9, 2018, 14 pages.

HYBRID TELESCOPE FOR OPTICAL BEAM DELIVERY AND RELATED SYSTEMS

CLAIM OF PRIORITY

The present application is a divisional of U.S. patent application Ser. No. 14/295,664, filed Jun. 4, 2014, which claims priority to U.S. Provisional Patent Application Ser. No. 61/830,820, filed Jun. 4, 2013, the disclosures of which are hereby incorporated herein by reference as if set forth in their entireties.

STATEMENT OF GOVERNMENT SUPPORT

This inventive concept was funded in-part with government support under Grant Applications ID R44EY018021-03 and ID 1R43EY022835-01 by the National Institutes of Health, National Eye Institute. The United States Government has certain rights in this inventive concept.

FIELD

The present inventive concept relates generally to scanning beam optical systems and, more particularly, to confocal imaging systems, optical coherence tomography imaging systems, laser delivery systems and the like.

BACKGROUND

Ophthalmic diagnostics and therapeutics frequently rely on a class of optical systems that involve the tailoring and delivering of a beam of optical radiation to a subject, for example, an eye. Lasers are used for ablation and photocoagulation, for example, in the treatment of tumors of the eye and vascular disease of the eye. The scanning laser ophthalmoscope is a direct-detection scanning beam confocal imaging technology designed to acquire high contrast images of the ocular fundus. High resolution scanning confocal microscopy is used for cornea endothelial cell counting. Optical coherence tomography is a low numerical aperture confocal interferometric imaging system for obtaining depth-resolved images of ocular structure.

Each of these systems typically requires tailoring of beam geometries to achieve specific objectives. Generally, focal control is required to direct the beam waist of the optical radiation to the region of interest, and beam magnification controls numerical aperture for lateral resolution at the beam waist and depth of field around the beam waist. Existing beam delivery systems may be improved.

SUMMARY

Some embodiments of the present inventive concept provide an optical coherence tomography (OCT) imaging system including a source of broadband optical radiation coupled to a sample arm of the OCT imaging system; a beam shaping optical assembly in the sample arm of the OCT imaging system, the beam shaping optical assembly being configured to receive optical radiation from the source as a beam of optical radiation and to shape the spatial profile of the beam of optical radiation; a scan mirror assembly coupled to the beam shaping optical assembly in the sample arm of the OCT system; and objective lens assembly coupled to the beam shaping optical assembly. The beam shaping optical assembly comprises a lens assembly configured to change a numerical aperture (NA) of the OCT system without changing a focus of the OCT system; to change a focus of the OCT system without changing a NA of the system; or to change both the NA and the focus of the OCT system responsive to a control input.

In further embodiments of the present inventive concept, the beam shaping optical assembly may include a hybrid telescope (HT). The HT may include a first positive lens following the collimator; a second, movable, negative lens following the first positive lens; and a third, moveable, positive lens following the second movable, negative lens and preceding the scan mirror assembly.

In still further embodiments of the present inventive concept, the OCT imaging system may further include a controller configured to move lenses within the beam shaping optical assembly lenses in response to a command to adjust the NA or focus. The controller may include one of a piezo translator and a stepper motor. The controller may be controlled by a user external to the system.

In some embodiments, the OCT system may further include an objective lens assembly for imaging an eye. The system including the beam shaping optical assembly, the objective lens assembly and any additional optical elements between the beam shaping optical assembly and the objective lens assembly may have a total focal power range of 60 Diopters (D) and may operate between +30 to −30 D and wherein the numerical aperture may be adjustable over at least a factor of 2. The system may be configured to deliver optical beam diameters at the cornea between about 2 mm to about 6 mm.

In further embodiments, the OCT system may be adjustable to operate with a total focal power between +60 to −30 D.

In still further embodiments, the objective lens assembly may further include an objective lens set following the scan mirror assembly, wherein the HT provides a range of focusing powers between +40 to −20 D and wherein the objective lens set provides an additional focusing range of +20 to −10 D.

In some embodiments, the OCT system may further include a beam expander following the scan mirror assembly. The dimensions of mirrors in the scan mirror assembly may be from about 3 mm to about 6 mm In further embodiments, the objective lens assembly may further include an objective lens set that does not require focusing.

Still further embodiments of the present inventive concept provide an optical scanning beam system including a collimator configured to receive an optical fiber couple to a source of the system; a scan mirror assembly coupled to the collimator of the system; and a focal assembly preceding the scan mirror assembly of the system between the collimator and the scan mirror assembly, wherein the focal assembly is configured to change a numerical aperture (NA) of the system, a focus of the system or both the NA and the focus responsive to a control input.

Some embodiments of the present inventive concept provide a controller for an optical coherence tomography (OCT) imaging system, the imaging system including a collimator in a sample arm of the OCT configured to receive an optical fiber couple to a source of the OCT system, a scan mirror assembly coupled to the collimator in the sample arm of the OCT system a hybrid telescope preceding the scan mirror assembly in the sample arm of the OCT system between the collimator and the scan mirror assembly. The controller includes a means for controlling two or more lenses of the hybrid telescope. The HT comprises a first positive lens following the collimator; a second, movable, negative lens following the first positive lens; and a third, moveable, positive lens following the second movable, negative lens and preceding the scan mirror assembly. The means for controlling includes means for controlling the second, movable, negative lens, the third moveable, positive lens or both to change a numerical aperture (NA) of the system, a focus of the system or both the NA and the focus responsive to a control input of the controller.

Further embodiments of the present inventive concept provide methods for operating a scanning beam system. The method includes setting a hybrid telescope (HT) to a long focal length and a low numerical aperture (NA) upon entry into a region of interest in a sample; identifying a structure of interest within the region of interest of the sample; increasing the NA, reducing a depth of field and increasing brightness of a focal plane; and varying a focal length such that the focal length matches a working distance of a tool associated with the scanning beam system.

Still further embodiments of the present inventive concept provide optical scanning beam systems including an input source of optical radiation configured to transmit an optical beam having an initial beam diameter and a beam divergence; a beam conditioning assembly having an input configured to receive the optical radiation from the input source, a means for altering the beam diameter and the beam divergence, and an output configured to direct the optical radiation to a means for steering a beam of optical radiation along at least one direction orthogonal to a direction of beam propagation; a means for directing the steered beam of optical radiation to a region of interest associated with a subject; a means for collecting at least a portion of the optical radiation that scattered from or transmitted through the region of interest; a means for detecting the collected optical radiation; a means for processing the detected optical radiation to produce an image derived from an attribute of the region of interest responsive to an interaction of the beam of optical radiation with the subject; a controller in communication with the beam conditioning assembly configured to control at least two motional degrees of freedom of the beam conditioning assembly, wherein the controller is configured to set the optical scanning beam system to one of a multiplicity of prescribed focus positions at fixed system numerical aperture and to set the optical scanning beam system to one of a multiplicity of prescribed numerical apertures at a fixed focal position.

DETAILED DESCRIPTION OF EMBODIMENTS

Figure 1A:
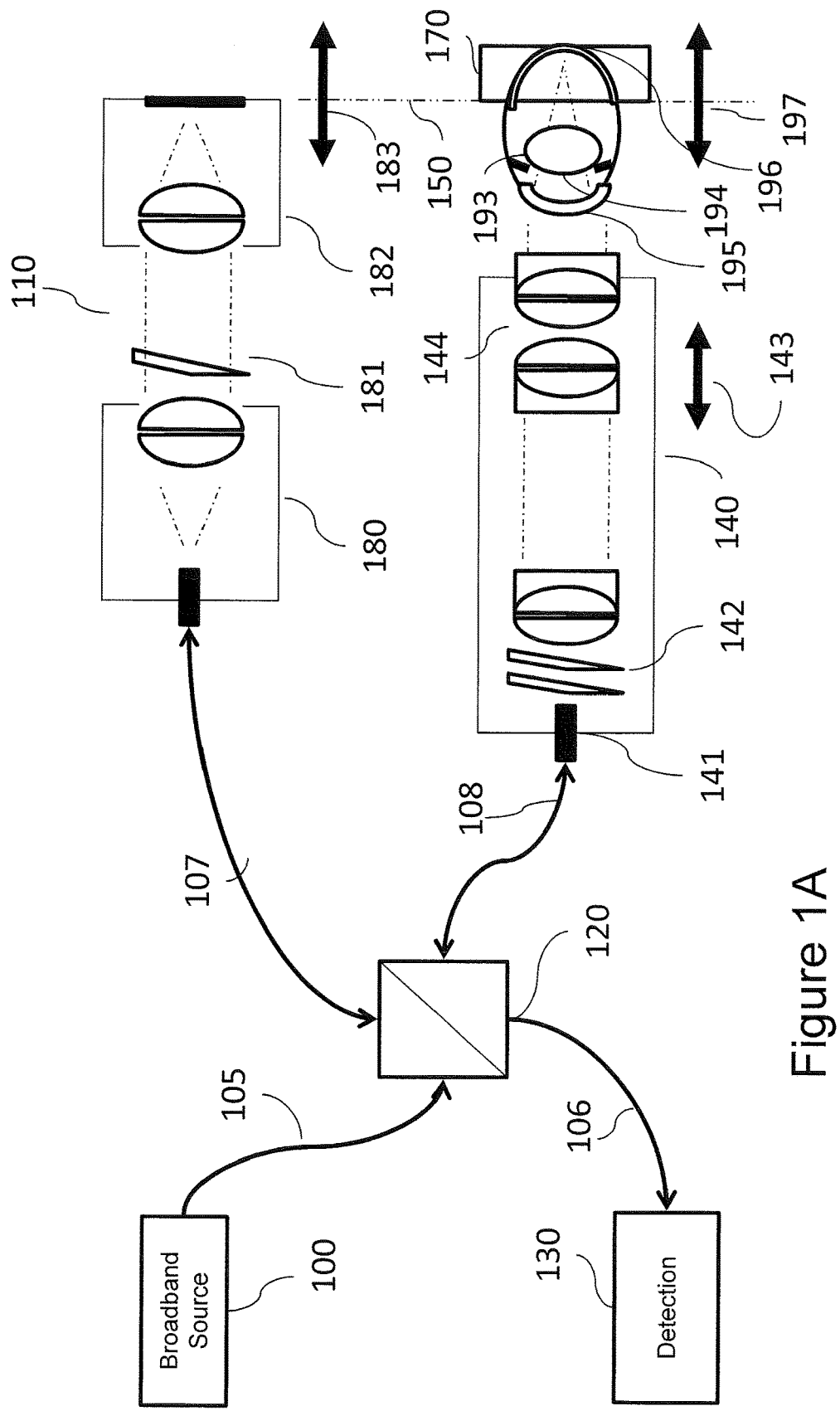
FIG. 1A is a block diagram illustrating an example Optical Coherence Tomography (OCT) retinal (posterior) imaging system.

The present inventive concept will be described more fully hereinafter with reference to the accompanying figures, in which embodiments of the inventive concept are shown. This inventive concept may, however, be embodied in many alternate forms and should not be construed as limited to the embodiments set forth herein.

Accordingly, while the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept as defined by the claims. Like numbers refer to like elements throughout the description of the figures.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this inventive concept belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

Although many of the examples discussed herein refer to the sample being an eye, specifically, the retina, cornea, anterior segment and lens of the eye, embodiments of the present inventive concept are not limited to this type of sample. Any type of sample that may be used in conjunction with embodiments discussed herein may be used without departing from the scope of the present inventive concept.

As used herein, the term "assembly" may refer to a single element, multiple elements and one or more lens sets without departing from the scope of the present inventive concept. Thus, for example, the term objective lens assembly may refer to more than the lens or lenses includes in the objective lens set.

Imaging and specifically OCT imaging is discussed in commonly assigned U.S. patent application Ser. No. 13/705,867 entitled Optical Imaging Systems Having Input Beam Shape Control and Path length Control; and U.S. patent application Ser. No. 13/836,576 entitled Surgical Microscopes Using Optical Coherence Tomography and Related Systems and Methods, the disclosures of which are incorporated herein by reference as if set forth in their entirety.

Ophthalmic diagnostics and therapeutics frequently rely on a class of optical systems that involve the tailoring and delivering of a beam of optical radiation to a subject, for example, an eye. For example, lasers are used for ablation and photocoagulation, for example, in the treatment of tumors of the eye and vascular disease of the eye. The scanning laser ophthalmoscope is a direct-detection scanning beam confocal imaging technology designed to acquire high contrast images of the ocular fundus. High resolution scanning confocal microscopy is used for cornea endothelial cell counting. Optical coherence tomography is a low numerical aperture confocal interferometric imaging system for obtaining depth-resolved images of ocular structure.

Each of such systems typically requires tailoring of beam geometries to achieve specific objectives. Generally, focal control is required to direct the beam waist of the optical radiation to the region of interest, and beam magnification controls numerical aperture for lateral resolution at the beam waist and depth of field around the beam waist. As used herein, "beam waste" refers to the position of the minimum diameter of a focused optical beam, for example, as defined by Gaussian optics known to those having skill in the art. An ideal beam delivery system would be adaptable to tailor characteristics for the various applications and regions of interest. An ideal beam delivery system would have the following set of attributes: variable numerical aperture to control the distribution of radiation over a depth of field and to allow control of lateral resolution at the position of focus; variable focus to allow independent control of a focal position relative to a region of interest; path length constancy to reduce positional changes between the system and the subject, and in the case of interferometric systems to reduce changes to path matching conditions; and adjustability to accommodate a wide range of final objectives, to provide versatility for various procedures.

As discussed above, existing systems do not address all of the desired set of attributes. In most related imaging systems, numerical aperture is nominally fixed by design, and focus is controlled through mechanical motion of one or more distal lens groups or elements. Such systems typically require mechanical control of relatively large and heavy optical subsystems, in proximity to the subject. In scanning retinal imaging systems, such focal control can impact the working distance to the subject, the relay of the scanning conjugate to the entrance pupil of the eye, and the path matching condition for optical coherence tomography.

A Keplerian telescope system utilizing two positive lens groups displaced by the sum of their respective focal lengths is sometimes incorporated in such beam delivery systems, and the relative distance between the two optical lens groups can be used introduce a degree of optical focal power to the nominally afocal zoom. Such a control system necessarily couples numerical aperture to focal power, and such coupling is not desirable for precision applications.

A Galilean telescope system utilizing one positive lens group and one negative lens group has an advantage of providing an upright image, and has found use in certain visual systems. A Galilean telescope has a limited field of view and is not in general use in optical beam delivery systems.

Thus, embodiments of the present inventive concept provide for a focal and numerical aperture control system that allows independent control of numerical aperture and focusing power over a useful range, while maintaining path length constancy, and flexibility to adapt to various final objective lenses as will be discussed further herein with respect to the Figures.

There are non-imaging scanning beam optical systems that have achieved some, but not all, of the target attributes of the present inventive concept. For example, U.S. Pat. No. 5,220,450 entitles Scanning Optical System Capable of Automatic Focus discusses a scanning beam system with focus control and with a means for detecting such focus control for a laser plotter application. Focal control implementations with both Keplerian and Galilean systems are proposed. Numerical aperture control is not discussed. U.S. Pat. No. 6,426,840 entitled Electronic Spot Light Control discloses a sequential beam control system with a first set of optics for adjusting the spot size of a beam and a second set of optics for adjusting a focus position of that beam for use in stereolithography systems. The primary objective of this inventive concept is to control the asymmetry in beam dimension associated with a solid state laser spot that leads to astigmatism in focus rather than to control the numerical aperture of the system. U.S. Pat. No. 6,451,010 entitled Zoom Handpiece for Laser Surgery discusses a beam condition system including a Galilean telescope to manage the beam diameter at a fixed working distance through focal control only. As the focal power is increased the focal length decreases. At a fixed working distance, the beam expands away from the focus towards the subject thereby increasing the beam diameter at the subject.

While each of these beam delivery examples utilizes a beam conditioning system incorporating a Keplerian zoom, a Galilean zoom or a combination thereof, each system is targeted at delivering a beam to a target surface with an emphasis on focal distance, beam astigmatism or spot size at the target. None of these conventional systems provide for an imaging system, or an imaging system with an independent focal control for controlling the location of a beam waist at or within the object to be imaged and independently controlling the numerical aperture to manage the depth of field of the acquired image. Specifically, none of the conventional systems discusses how to condition a scanning beam to independently control a position of a beam waist, the diameter of a beam waist, and the resultant depth of field around the beam waist for acquiring an image by detecting backscattered or transmitted light from the conditioned beam that has interacted with the subject.

Accordingly, some embodiments of the present inventive concept provide a scanning beam imaging system comprising an input source of optical radiation, directing the input radiation through a beam conditioning subsystem whereby the beam conditioning subsystem provides a means for independent control of a position of the beam waist, or focus, of the imaging system, and the beam diameter at focus, and consequently the numerical aperture or depth of field of the imaging system. The scanning beam imaging system may further include a means for scanning the conditioned beam along at least one axis orthogonal to the beam axis, a means for directing the scanning conditioned beam to a region of interest at or within a sample, a means for receiving either backscattered optical radiation or transmitted optical radiation from the sample and directing this backscattered or transmitted optical radiation to a further means for detecting this radiation, and a means for constructing a signature or an image of the region of interest of the subject. These scanning beam imaging systems may include additional optics between the scanning means and the subject for further conditioning of the scanned beam as appropriate to the subject and imaging requirements as will be discussed further herein with respect to the figures.

Examples of such scanning imaging systems include an imaging system using direct detection or coherent interferometric detection. For example, such scanning imaging systems may include without limitation, a low coherence interferometry topography or tomography system, an optical coherence tomography (OCT) imaging system, a scanning laser ophthalmoscope (SLO) imaging system, a scanning confocal microscopy imaging system, and a scanning endoscopic imaging system. Furthermore, an OCT imaging system may be directed towards living or non-living samples, and may include ocular or non-ocular structures. An ophthalmic imaging system according the present inventive concept may include a system for imaging anterior structures of the eye including a cornea, an iris, an irideocorneal angle, natural or ersatz lens of the eye, a posterior region or structure of the eye, such as a retina, or any other internal or external structure of the eye.

Further applications of such scanning imaging systems may include, without limitation, systems for imaging with a variable defined position of focus or variable defined f-number (or numerical aperture or depth of field) in order to control a position of the image and a depth of field of an image. As used herein, an "f-number" refers to the ratio of the focal length to the diameter of the entrance pupil of the optical system, and is inversely proportional to the system numerical aperture (NA). The focus control may include continuous control over an available range of focus or may include focus by discrete values. Similarly, the f-number or numerical aperture control may include a continuous control or a control by a discrete set of values. The focal control may be accomplished without changing the system f-number, and the f-number may be changed without changing the position of system focus.

For ophthalmic retinal imaging applications, the focal control may be of sufficient range to accommodate a range of refractive errors for the myopic, hyperopic or aphakic eye, and may include a sufficient focal range to allow imaging from the cornea to the retina. As used herein, "myopic" refers to the clinical condition of nearsightedness; "hyperopic" refers to the clinical condition of farsightedness; and "aphakic" refers to the absence of a natural or replacement intraocular lens in the eye of a subject.

Some embodiments of the present inventive concept provide a hybrid Galilean-Keplerian telescope (hybrid telescope, HT) including a first lens group having a first optical power or effective focal length, followed by a second lens group have a second optical power, the second lens group having a negative optical power, followed by a third lens group having a third positive optical power. The specific optical properties, for example, clear aperture, focal length, and aberration correction, of each lens group may be tailored to specific requirements of the optical system. The relative position between the lens groups may be controlled, for example, by displacing the second, negative, lens group with the respect to the first lens group and displacing the third, positive, lens group with respect to the second in order to modify the optical power, and numerical aperture of this hybrid Galilean-Keplerian telescope system.

A scanning retinal imaging system will be discussed that highlights some of the attributes and performance advantages of the HT in accordance with embodiments of the present invention concept. Referring first to FIG. 1A, a block diagram of a conventional retinal OCT imaging system will be discussed. As illustrated in FIG. 1A, the system includes a broadband source 100 delivered over a source path 105 that may include an optical fiber, a reference arm 107 and a sample arm 108 coupled to each other by a beamsplitter 120. The beamsplitter 120 may be, for example, a fiber optic coupler or a bulk or micro-optic coupler. The beamsplitter 120 may provide from about a 50/50 to about a 90/10 split ratio. As further illustrated in FIG. 1A, the beamsplitter 120 is also coupled to a wavelength or frequency sampled detection module 130 over a detection path 106 that may be provided by an optical fiber.

The sample arm 108 couples an optical fiber to an optical assembly that shapes the spatial profile of the beam of optical radiation emitted from the optical fiber. The optical assembly may commonly be specified as a collimator 141 at the input to the sample arm imaging optic 140 that delivers collimated light to a pair of scanning mirrors 142, through imaging lenses that include a final objective 144. For an emmetropic subject, the optical beam delivered from the optical fiber through final objective is collimated and at least nominally telecentric. As used herein, "emmetropic" refers to the clinical condition of normal uncorrected sight, i.e., the ability to focus on distant objects without supplemental correction; and "telecentric" refers to an optical system in which the chief rays are parallel to the optical axis across the field of view. The collimated light is focused through the cornea 195 and crystalline lens 193 of the subject to the retina 196. By imaging the scanning mirror assembly (scanning mirrors) 142 to the pupil 194 of the subject, the scanned beam pivots through the pupil to image the retinal plane with the minimum vignetting. In an OCT system, the resultant image is a depth resolved image of the subject in a window 170 related to the path matching condition 150 with the setting of the reference arm optics 110.

In the retinal imaging system of FIG. 1A, the eye focuses the beam onto the retina, the path matching condition is defined by the reference path length and the sample arm path length, including the length of the eye, and the lateral resolution and depth of field of the scanning beam are constrained by the diameter of the beam at cornea. A typical reference arm assembly 110 will have an input collimator 180, a variable optical attenuator 181, and a retroreflector assembly 182. The retroreflector may be coupled to a movable assembly 183 for adjustment to variations in eye length, or more generally to match the reference arm path length to the sample arm path position 197. Correction for refractive errors of the subject is generally addressed through one or more movable lens elements 143 associated with the objective lens group 144. It is frequently desirable to be able to image without mydriasis (dilation of the eye), constraining the beam diameter to less than about 3 mm.

Figure 1B:
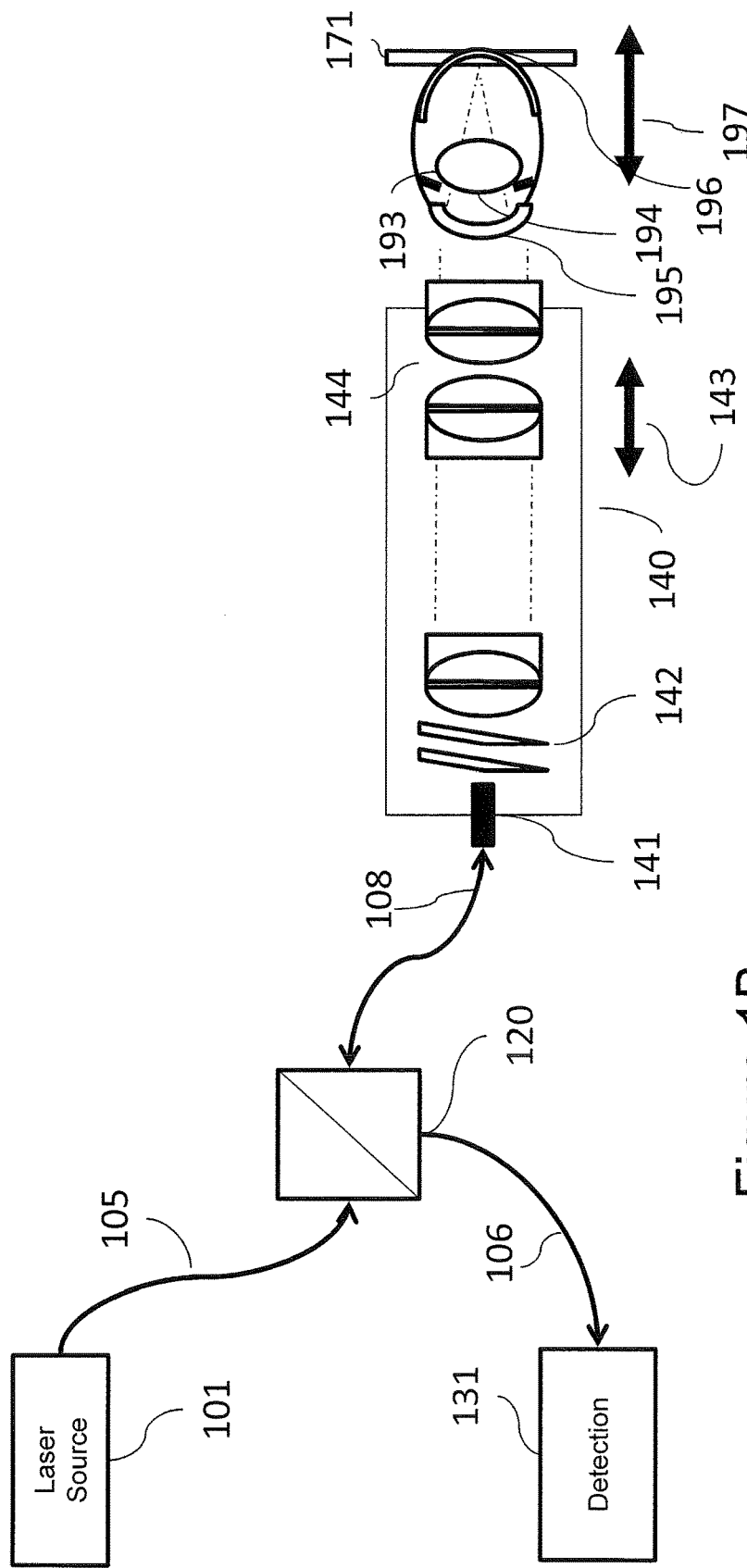
FIG. 1B is a block diagram illustrating a scanning laser ophthalmoscope (SLO) imaging system.

Referring now to FIG. 1B, another common retinal imaging system, a scanning laser ophthalmoscope (SLO), will be discussed. As illustrated in FIG. 1B, an SLO is quite similar to the OCT system of FIG. 1A. However, an SLO incorporates a direct detection system 131 instead of an interferometric detection system discussed with respect to the OCT system above. The SLO system does not have a reference arm. Furthermore, an SLO system typically uses a narrow linewidth laser source instead of a broadband source. Otherwise, the optical imaging attributes of an SLO system are nominally equivalent to an OCT system, except that the SLO system obtains a fundic image integrated over the confocal depth of field 171 instead of the depth-resolved image of the OCT system.

In both systems illustrated in FIGS. 1A and 1B, focal control is required, first to compensate in refractive deviations from emmetropia, and second to control the region of interest in imaging. Focal control in such scanning beam retinal imaging systems is generally accomplished through relative position control 143 of the final objective 144. This focal control impacts the conjugate of the scan mirrors 142 as well as the beam focus, and requires coordination of focus and working distance, and, for OCT, the reference arm path length.

Furthermore, it is often desirable to more precisely control the focus with respect to the surface of the retina. One may desire an emphasis on the inner retina, for example the nerve fiber layer; the outer retina, for example, the retinal pigment epithelium; or the choroid, or one may desire to image structures within the vitreous, for example, to observe vitreal traction or inflammatory processes associated with uveitis. As used herein, "uveitis" refers to a clinical condition of inflammation of the uvea, or middle portions of the eye. In some embodiments the focal control may be mediated without introducing vignetting or changing the working distance.

Additionally, it may be advantageous to increase the numerical aperture and improve the lateral resolution by increasing the incident beam size. With current systems, this may only be possible with a dilated pupil, and dilation is frequently available in a clinical or surgical exam. Current ophthalmic imaging systems do not offer the flexibility to modify the beam diameter for different circumstances.

Figure 2A:
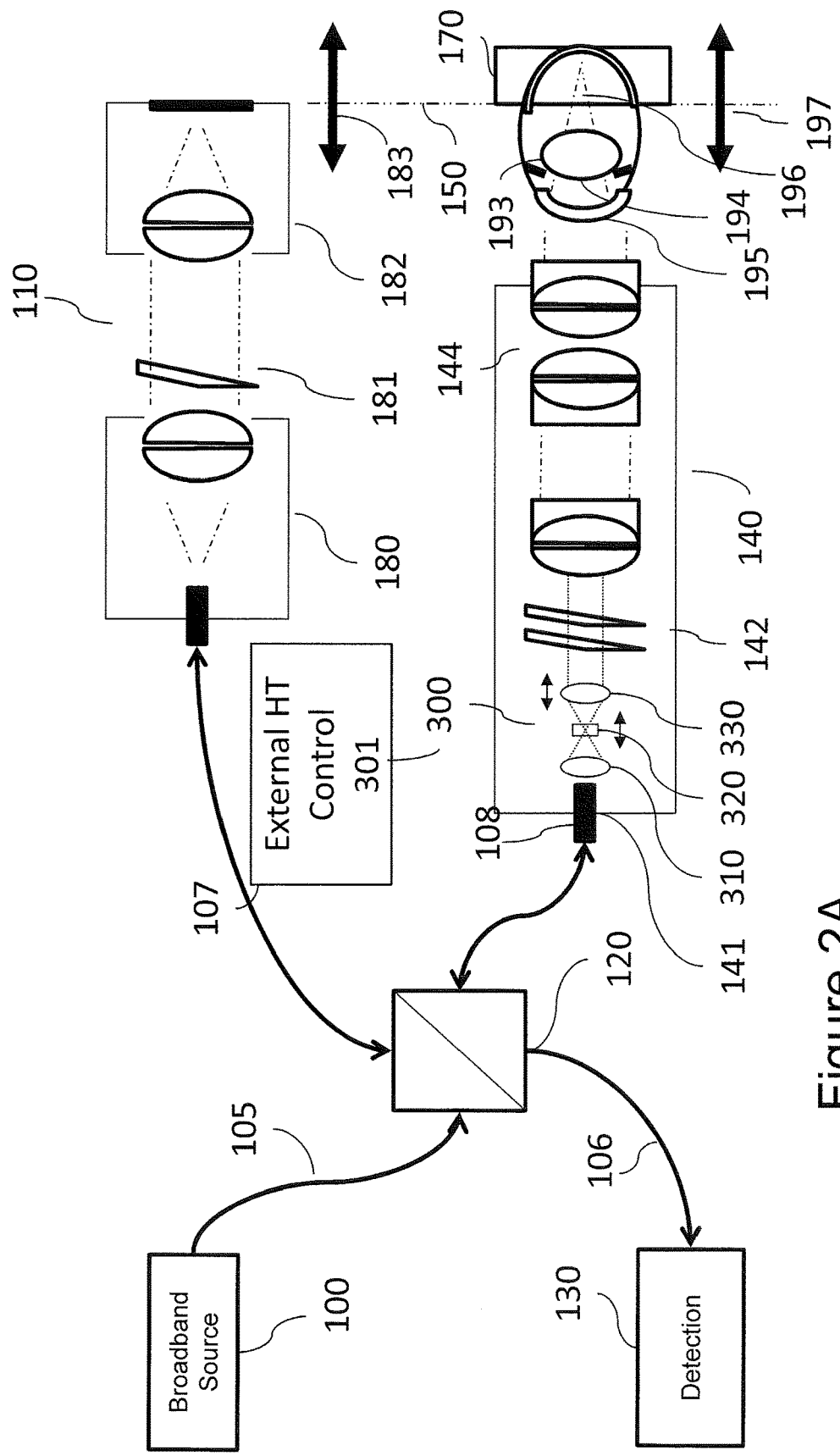
FIG. 2A is a block diagram of an imaging system including a hybrid telescope in accordance with some embodiments of the present inventive concept.

Embodiments of the present inventive concept address some of these shortcomings of conventions systems. Referring first to FIG. 2A, systems including a hybrid telescope (HT) in accordance with some embodiments of the present inventive concept will be discussed. As illustrated in FIG. 2A, in accordance with embodiments discussed herein, a HT 300 is inserted between the collimator 141 and the scan mirror assembly 142.

In some embodiments discussed herein, the portion of the system following the beam splitter 120 in the sample arm may be referred to as "a beam shaping optical assembly" in the sample arm 108 of the OCT imaging system. Thus, the beam shaping optical assembly in accordance with some embodiments may include the collimator 141 and the HT. As will be discussed below, the beam shaping optical assembly may be configured to receive optical radiation from the source as a beam of optical radiation and to shape the spatial profile of the beam of optical radiation.

Referring again to FIG. 2A, the HT may include first through third lenses 310, 320 and 330. As illustrated therein, the first positive lens 310 is followed by the second, movable, negative lens 320 and the third, movable, positive lens 330. These lenses may be driven by, for example, a piezo translator or stepper motor, and may have a range of a few millimeters to one hundred or more millimeters, with a precision of a few micrometers or one or more millimeters. An external HT controller 301 may be provided to allow adjustment of the NA and/or focus by moving the lenses of the HT 300.

Thus, in accordance with some embodiments of the present inventive concept, the beam shaping optical assembly includes a lens assembly that may be configured to change a numerical aperture (NA) of the OCT system without changing a focus of the OCT system; a focus of the OCT system without changing a NA of the system; or both the NA and the focus of the OCT system responsive to a control input.

Positioning the HT following a collimated input allows the HT to act as a lens with deterministic aperture and divergence that can readily be modeled through the rest of the optical system. Because the beam is tailored before the scanning system, objective lens focusing of the objective lens assembly may not be required, and focus and zoom may be controlled at fixed working distances and path length relative to the subject. Furthermore, focus may be controlled without impacting the conjugate of the mirrors at the pupil of the eye, so that imaging conditions may be changed with a minimum of adjustment with respect to the subject.

In these embodiments, objective lens focal control 191 of the objective lens assembly may be used if desired. This may be advantageous for controlling the scanning mirror conjugate in relation to the pupil of the subject, the utility of which is generally overlooked, but may be beneficial when the refracting power of the cornea or anterior chamber length are different from the conditions of the design.

In some embodiments of the present inventive concept, the ophthalmic imaging system 140 may be adjusted with the HT 300 for a range of focusing powers between +30D to −30D, with a 3× zoom to accommodate to beam diameters at the cornea from between about 2 mm to about 6 mm, such range effectively covering 100% of the range of refractive errors in the human population, while allowing for significant ability to image structures anterior to retina within the vitreous. As used herein, "vitreous" refers to the transparent gelatinous substance filling the region between the retina and the crystalline lens of the eye. The imaging system may be further adjusted to accommodate +60 D of refractive correction, as may be required in cases of aphakia and for certain non-human animal models, such as rodents.

Figure 2B:
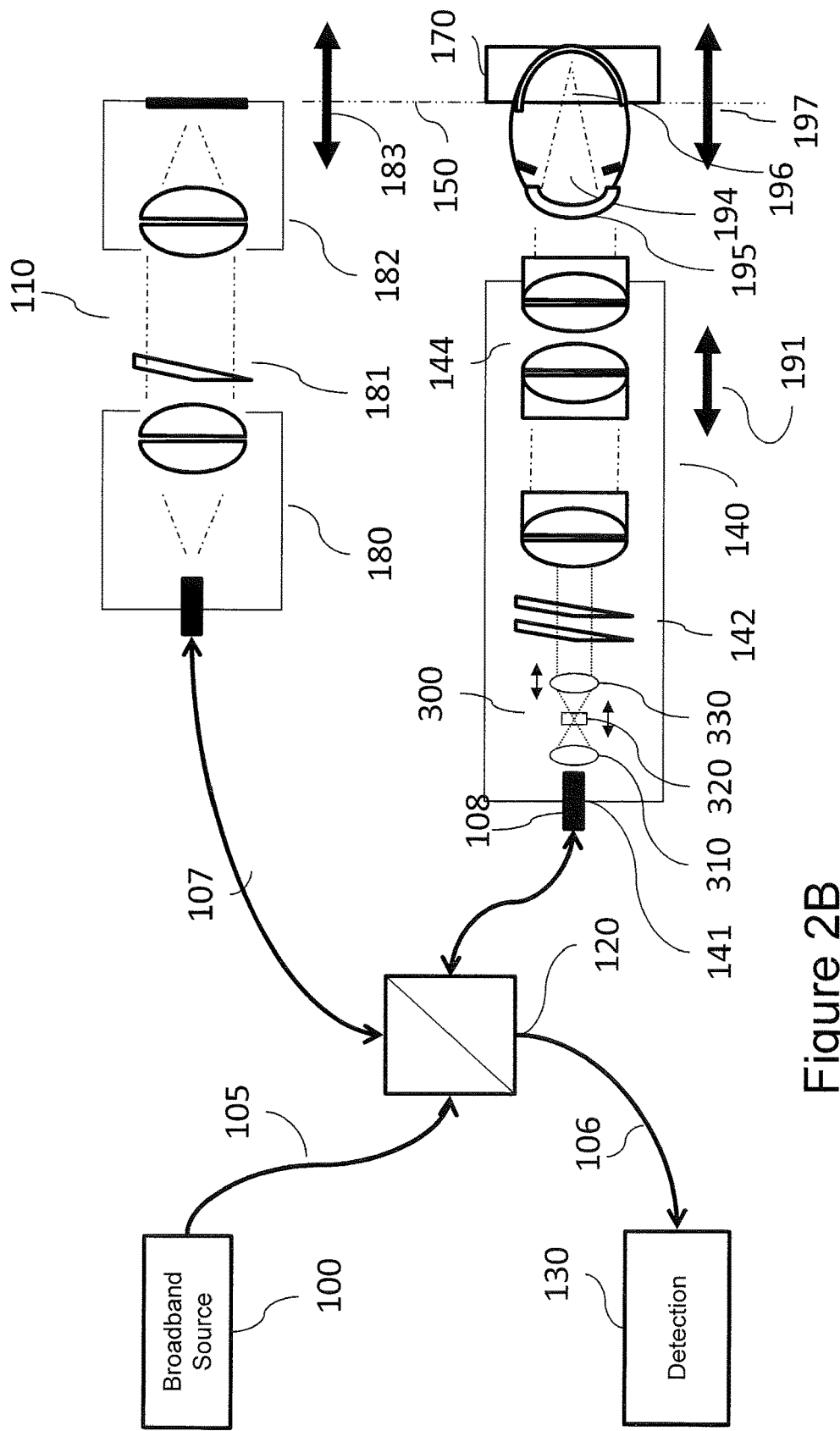
FIG. 2B is a block diagram of an imaging system including a hybrid telescope in accordance with some embodiments of the present inventive concept.

Aphakia, as discussed above, involves the absence of an ocular lens and is occasionally encountered in a subject. The lens of the eye contributes approximately +30 Diopters (D) to the refracting power of the eye. Imaging of an aphakic patient typically requires that the optical system substitute the optical power of the ocular lens. Thus, as shown in FIG. 2B, the subject eye is missing a natural or ersatz lens 194 (shown in FIG. 2A), and thus requires and additional level of focal power to successfully image the retina. In some embodiments of the present inventive concept, the HT 300 provides a range of focusing powers between +60 D to −30 D to accommodate an extended range of human and non-human refraction, including aphakia. In further embodiments of the present inventive concept, the HT 300 provides a range of focusing powers between +40 D to −20 D to accommodate the range of human refraction, including aphakia, while the final objective 144 provides a supplemental focusing range of +20 D to −10 D through relative motion 191 between elements of the objective lens group.

Although only some embodiments of the present inventive concept are discussed with respect to FIGS. 2A and 2B, additional embodiments may be envisioned that provide an appropriate balance between refraction and zoom capabilities of the HT and the objective lens for specific applications. Certain species are innately non-emmetropic, and the optical system may include a refractive bias. For example a rodent may nominally require 60 D to 90 D of focal power for retina imaging, and a rabbit may require 6 D. An optical system may thus include a bias for the nominal refraction of the subject, with HT offering a range of controls relevant to the species.

Figure 3:
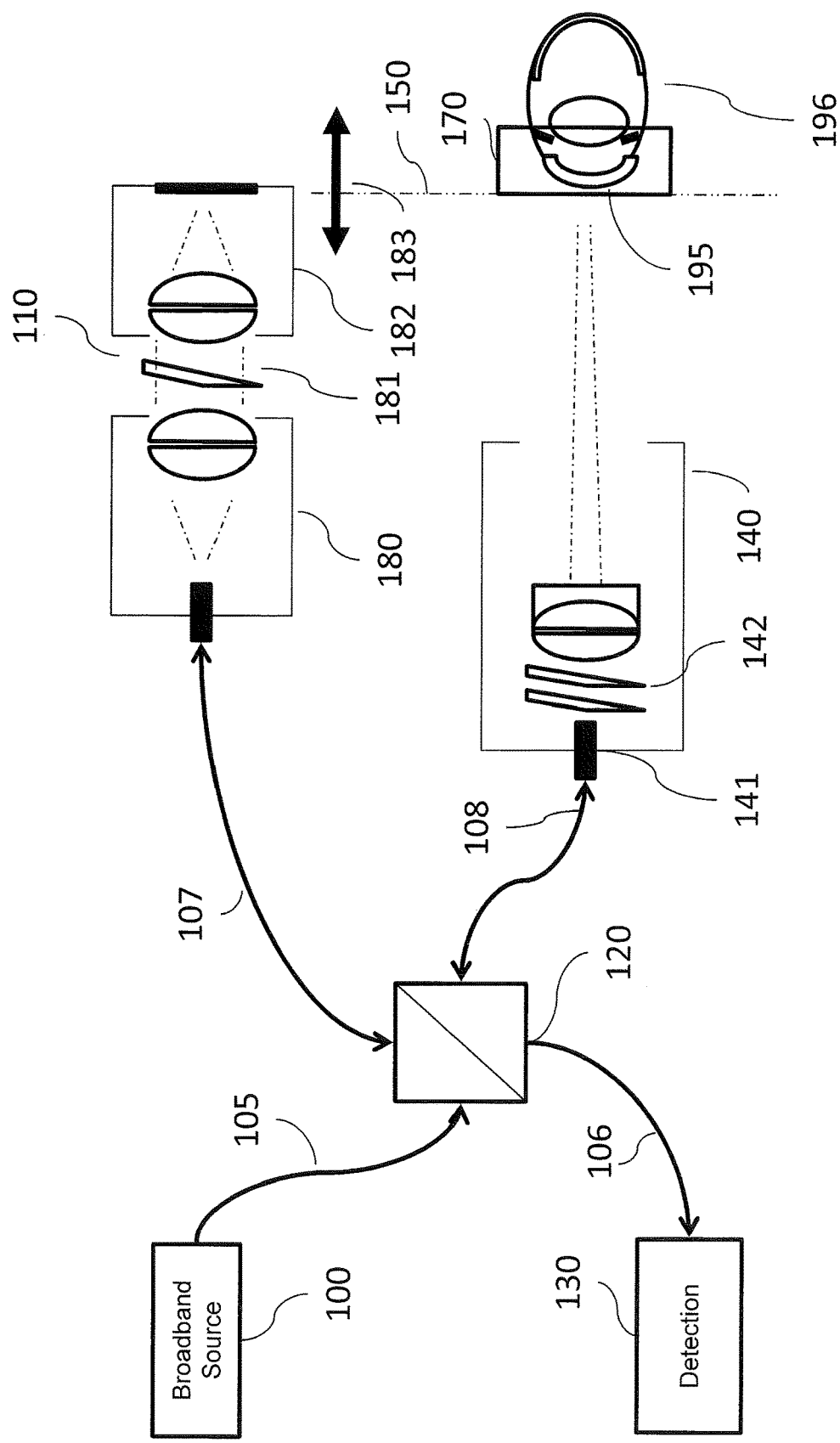
FIG. 3 is a block diagram illustrating an example Optical Coherence Tomography (OCT) cornea (anterior) imaging system.

Referring now to FIG. 3, a simple cornea imaging system will be discussed. Like reference numerals refer to like elements throughout. Therefore, details with respect to the elements of FIG. 3 discussed above with respect to FIGS. 1A and 1B will not be repeated herein in the interest of brevity. A cornea imaging system is typically a fixed focus, fixed numerical aperture system with a fixed resolution, magnification, field of view and depth of field. Different lenses may be adapted for changes in depth of field. Such a system, while indicated for cornea, may be used in many other applications where imaging through a constricted pupil, and therefore imaging a scan plane to a conjugate pupil, may not be required. Applications other than anterior ocular imaging may include, for example, dermal imaging.

Figure 4:
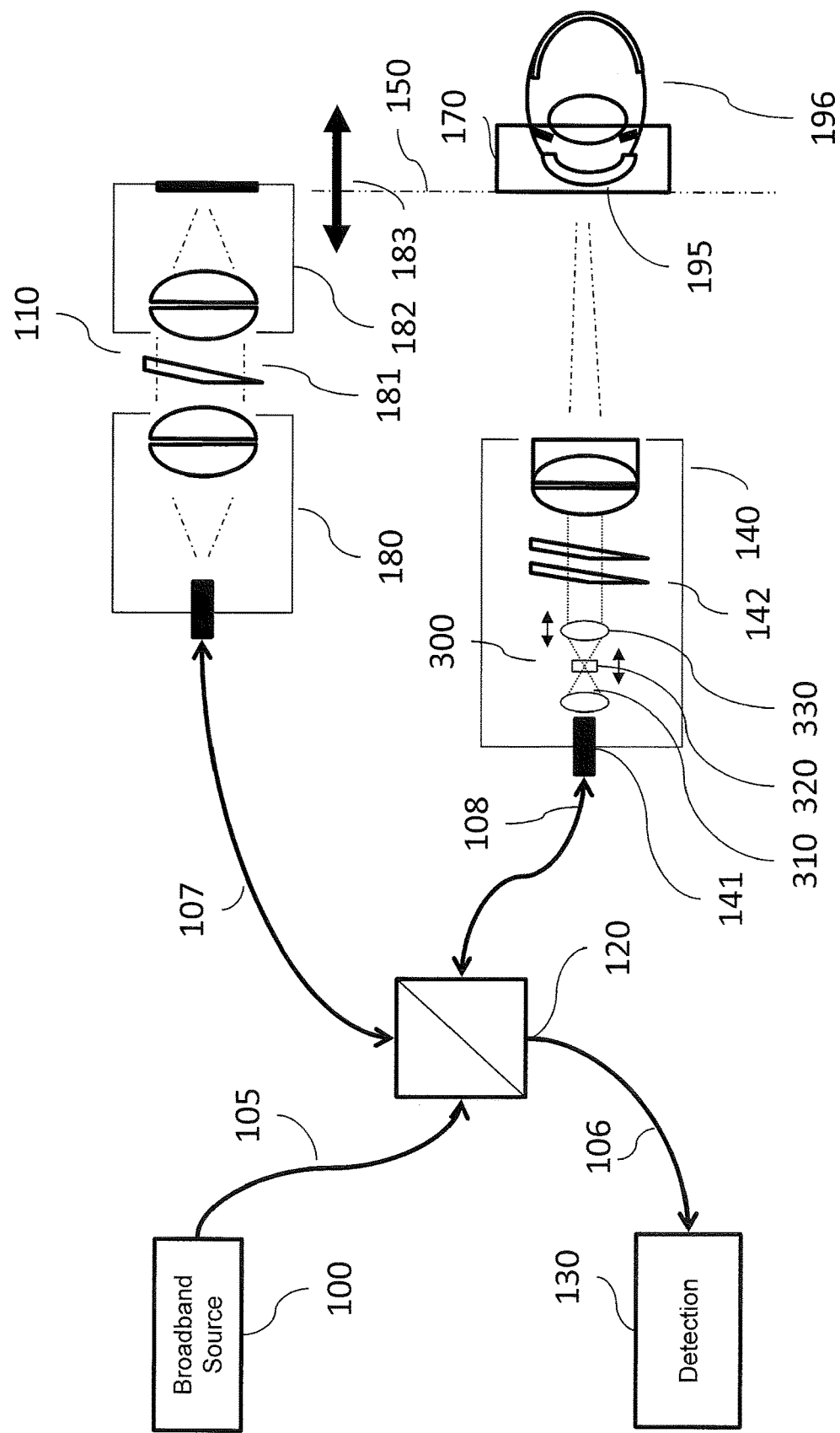
FIG. 4 is a block diagram of an anterior imaging system in accordance with some embodiments of the present inventive concept.

Referring now to FIG. 4, a block diagram of an imaging system in accordance with some embodiments of the present inventive concept utilizing focal and numerical aperture control for anterior ocular imaging will be discussed. Again, as discussed above, like reference numerals refer to like elements throughout. Therefore, details with respect to the elements of FIG. 4 discussed above will not be repeated herein in the interest of brevity. As illustrated in FIG. 4, a HT 300 according to embodiments of the present inventive concept is inserted between the collimator 141 and the scan mirror assembly 142. The first positive lens 310 is followed by the second, movable, negative lens 320 and the third, movable, positive lens 330. These lenses may be driven by, for example, a piezo translator or stepper motor, and may have a range of a few millimeters to ten or more millimeters, with a precision of a fraction or a millimeter. The HT 300 following a collimated input 141 acts as a lens with deterministic aperture and divergence that can readily be modeled through the rest of the optical system.

Figure 5:
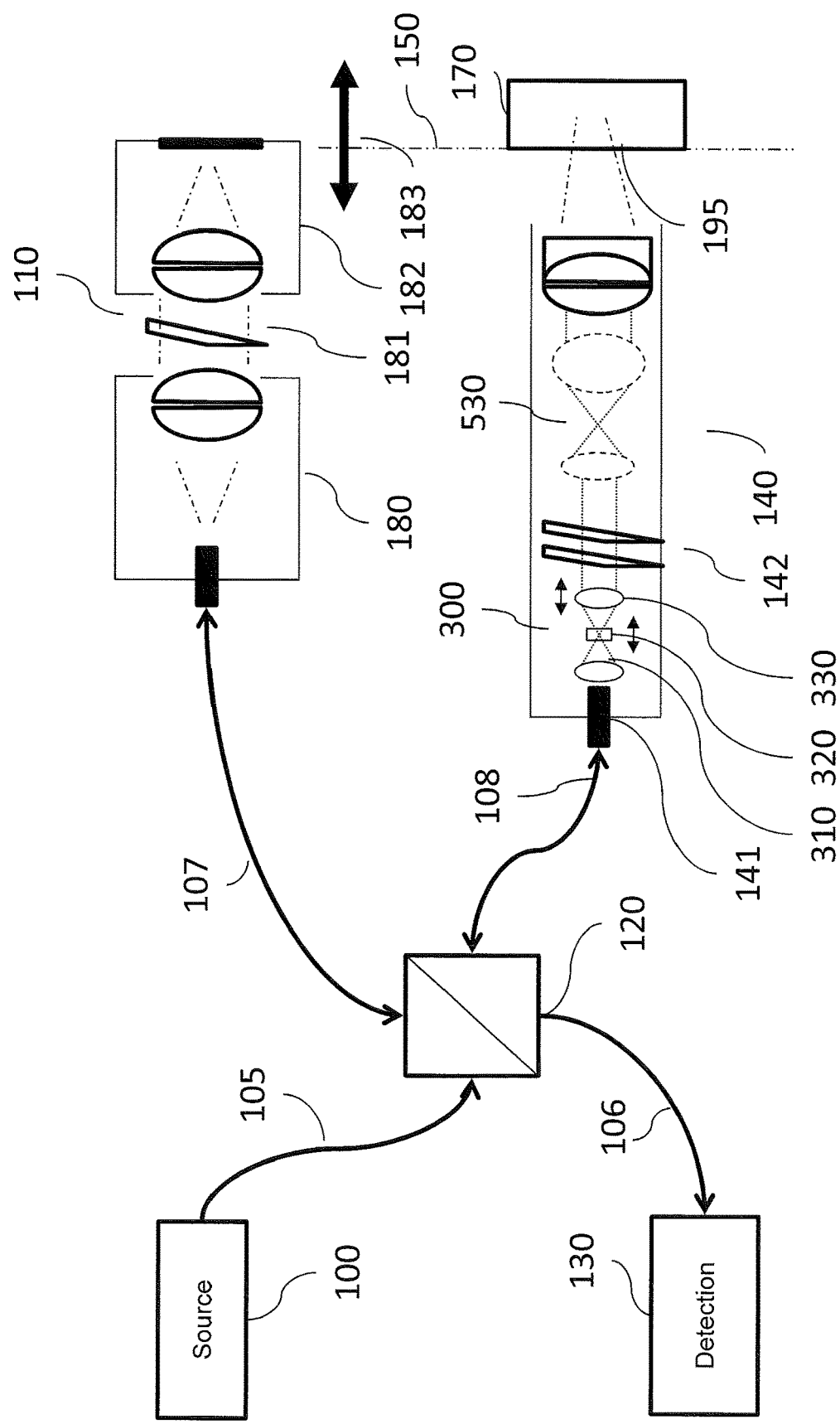
FIG. 5 is a block diagram of an anterior imaging system in accordance with some embodiments of the present inventive concept.

Referring now to FIG. 5, further embodiments of imaging systems in accordance with embodiments discussed herein will be discussed. Like reference numerals refer to like elements throughout. Therefore, details with respect to the elements of FIG. 5 discussed above will not be repeated herein in the interest of brevity. As illustrated in FIG. 5, a beam expander 530, which may be, for example, a Keplerian telescope, follows the HT 300, and in embodiments illustrated in FIG. 5, follows the scanning mirror 142. The geometry illustrated in FIG. 5 may provide the advantage of reducing the size of mirror required to achieve beam dimensions desired at the exit pupil of the system. For example, in the ocular imaging examples discussed it is often desirable to keep the mirror dimensions below 6 mm, and often at or below 3 mm. In such circumstances, a 3×5× zoom relay may be advantageous.

More generally, it may also be desirable to provide an endoscope for many applications, including laparoscopy in medical imaging and boroscopes for industrial imaging. The use of the HT 300 at the input end of the endoscope followed by a scanning system with miniature scanners, for example, micro-electro-mechanical systems (MEMS) scanners with mirrors as small as 1.0 mm, and followed by one or more relay telescopes with desired magnifications can provide a very useful endoscope with variable focal distance and depth of field for both direct and interferometric detection implementations.

Figure 6:
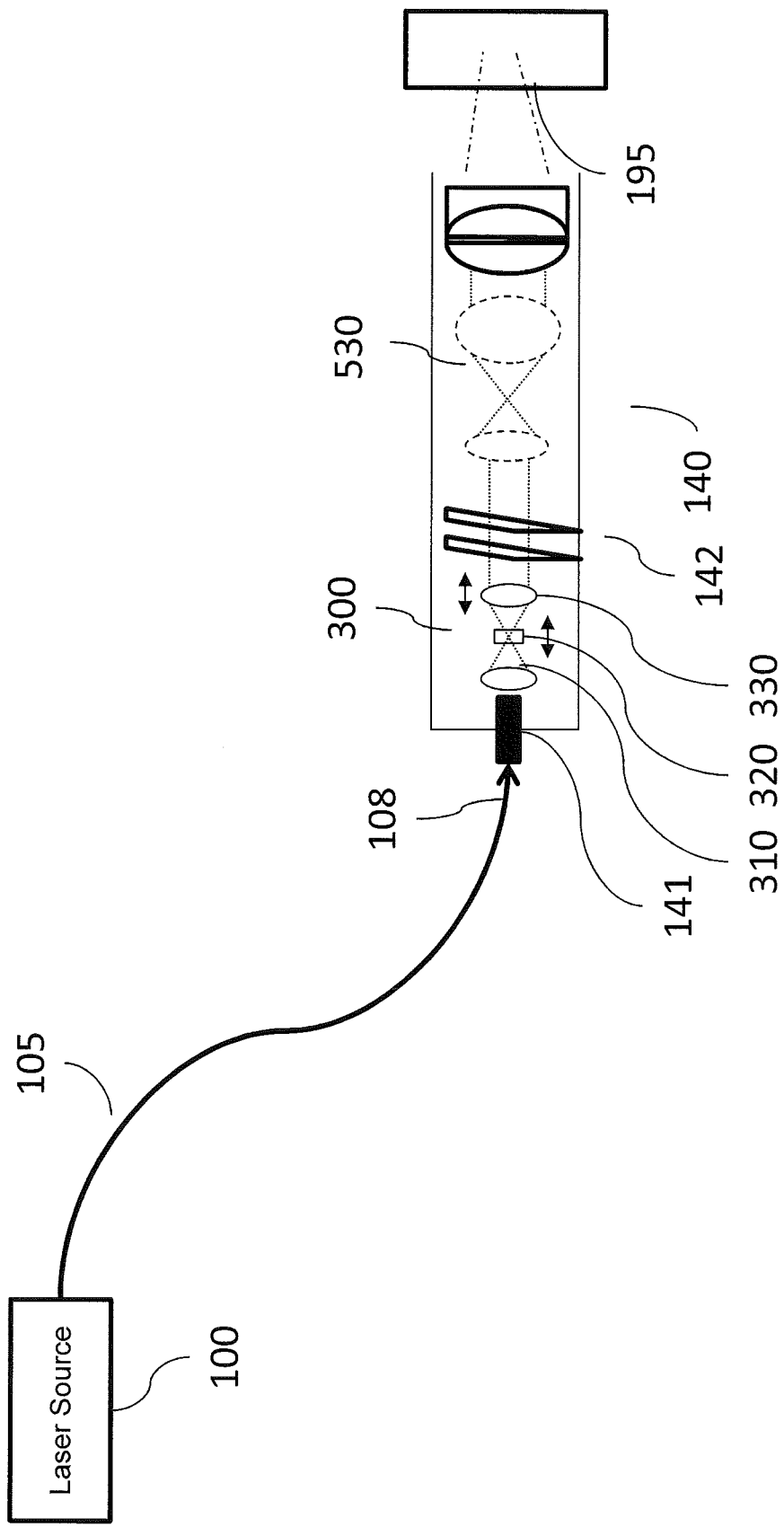
FIG. 6 is a block diagram of a laser delivery system in accordance with some embodiments of the present inventive concept.

Referring now to FIG. 6, a non-imaging application including the HT 300 in accordance with embodiments of the present inventive concept will be discussed. FIG. 6 illustrates a laser delivery application. For therapeutic laser delivery applications it is highly desirable to control both the position of maximum intensity (focus) and the intensity of the beam (beam waist). The HT 300 in accordance with embodiments of the present inventive concept positioned in the laser delivery system allows control of both maximum intensity and beam waist. Thus, embodiments of the present inventive concept may be used with scanning or non-scanning geometries, and with or without following relays or beam expanders.

Figure 7A:
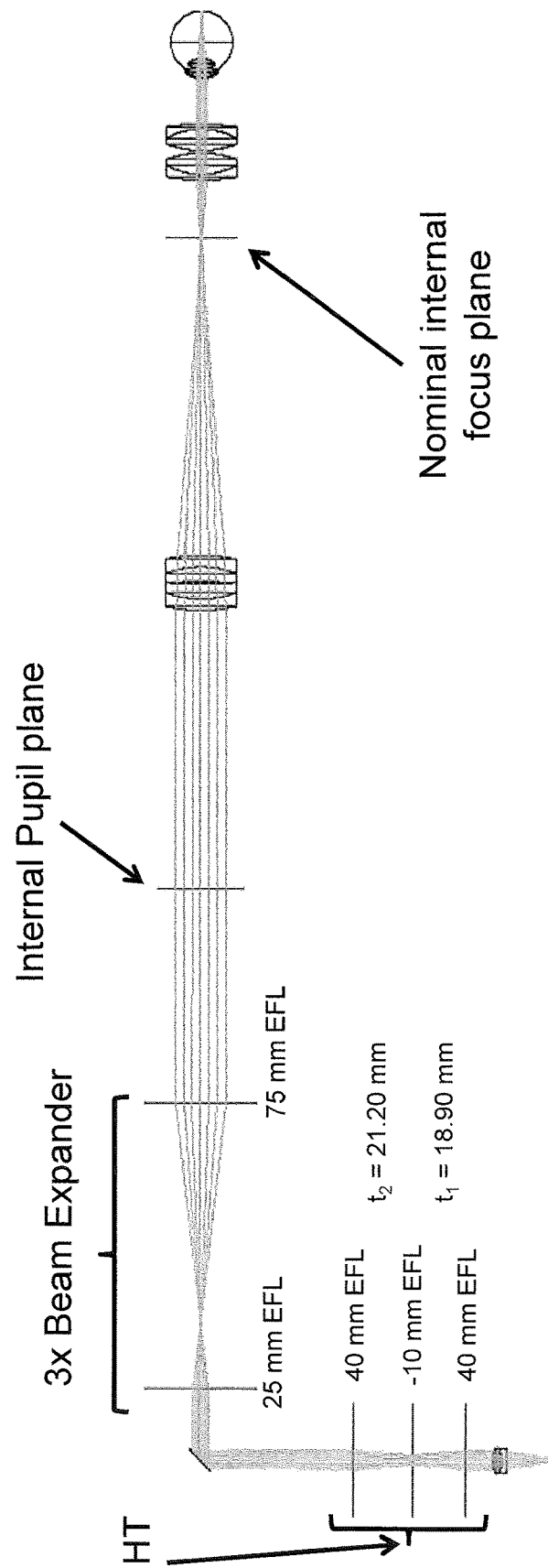
FIGS. 7A through 7G are diagrams illustrating a retinal imaging systems using a hybrid telescope in accordance with some embodiments of the present inventive concept.

Referring now to FIGS. 7A-7F, systems including a HT in accordance with embodiments of the present inventive concept will be discussed. In particular, a specific implementation of a retinal imaging system using a HT with 3× relay beam expander, a full focal range of +30D to −30D, and a 3× magnification range will be discussed with respect to FIGS. 7A-7F. To summarize the retinal imaging system in accordance with embodiments discussed herein, at low numerical aperture (NA) the beam diameter at focus is 13.5 µm. At high numerical aperture, the beam diameter is reduced to 4.5 µm. In the figures, the HT lens powers and separations t1 and t2 are discussed for each of six operating conditions at the range of performance of the system. As illustrated in the figures, the positive lens groups of the HT have the same 40 mm effective focal lengths (EFL), equivalent to +20 Diopters. The intermediate negative lens has an effective focal length of −10 mm, equivalent to −100 Diopters. The lens separation at maximum beam diameter (maximum numerical aperture, minimum f-number) is t1=18.90 mm between lens groups one and two, and t2=21.20 mm between lens groups two and three as illustrated in FIG. 7A. It will be understood that although lens powers and separations may be configured to achieve comparable results; the particular lens combinations are not a unique solution and embodiments of the present inventive concept are not limited thereto.

Figure 7B:
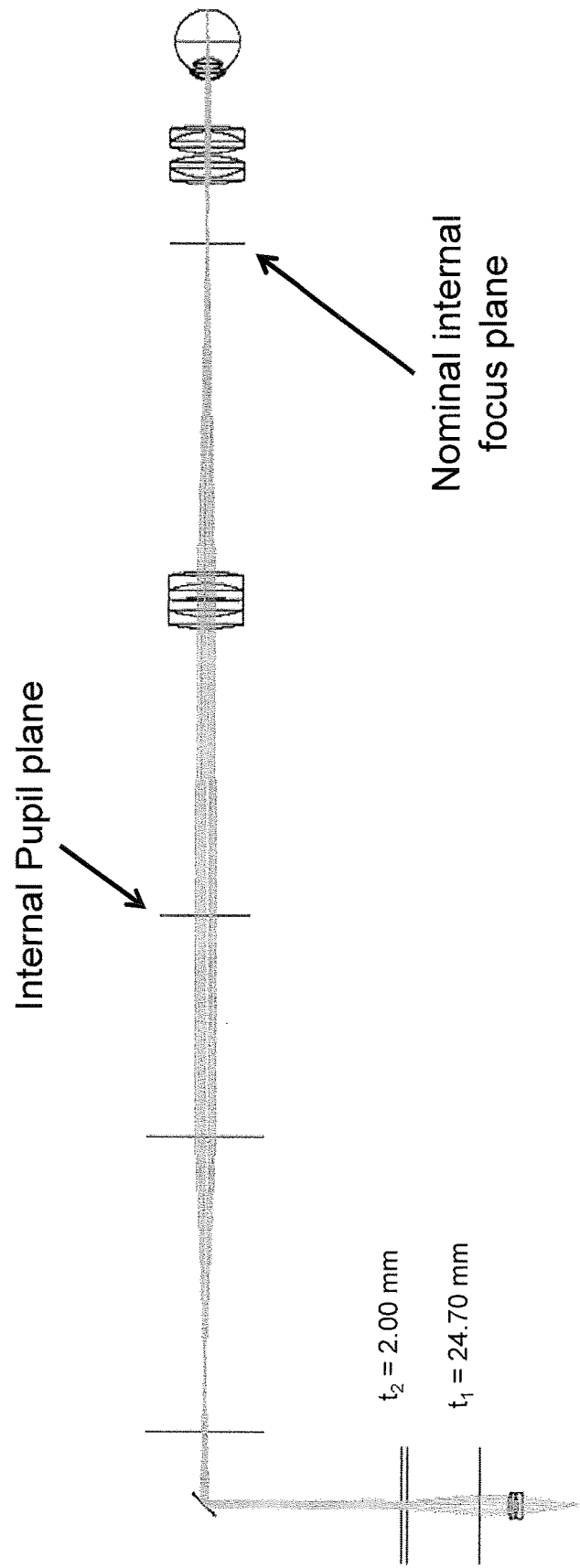
Figure 7C:
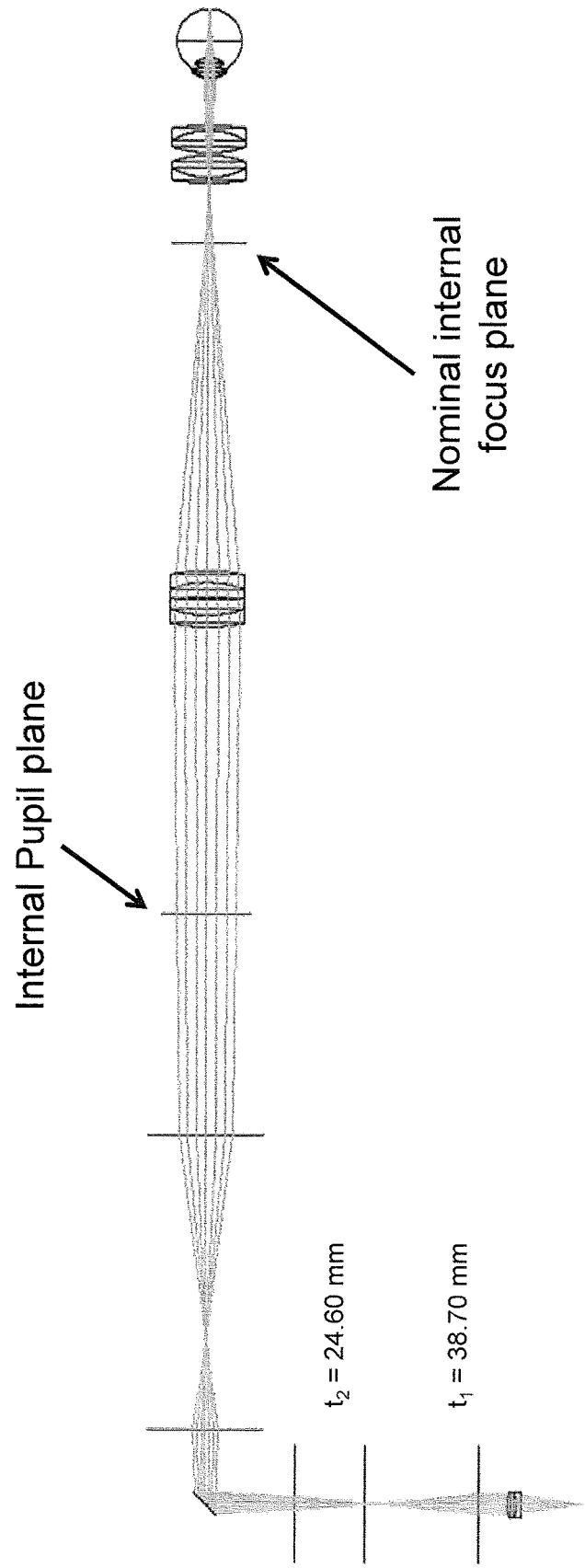
Figure 7D:
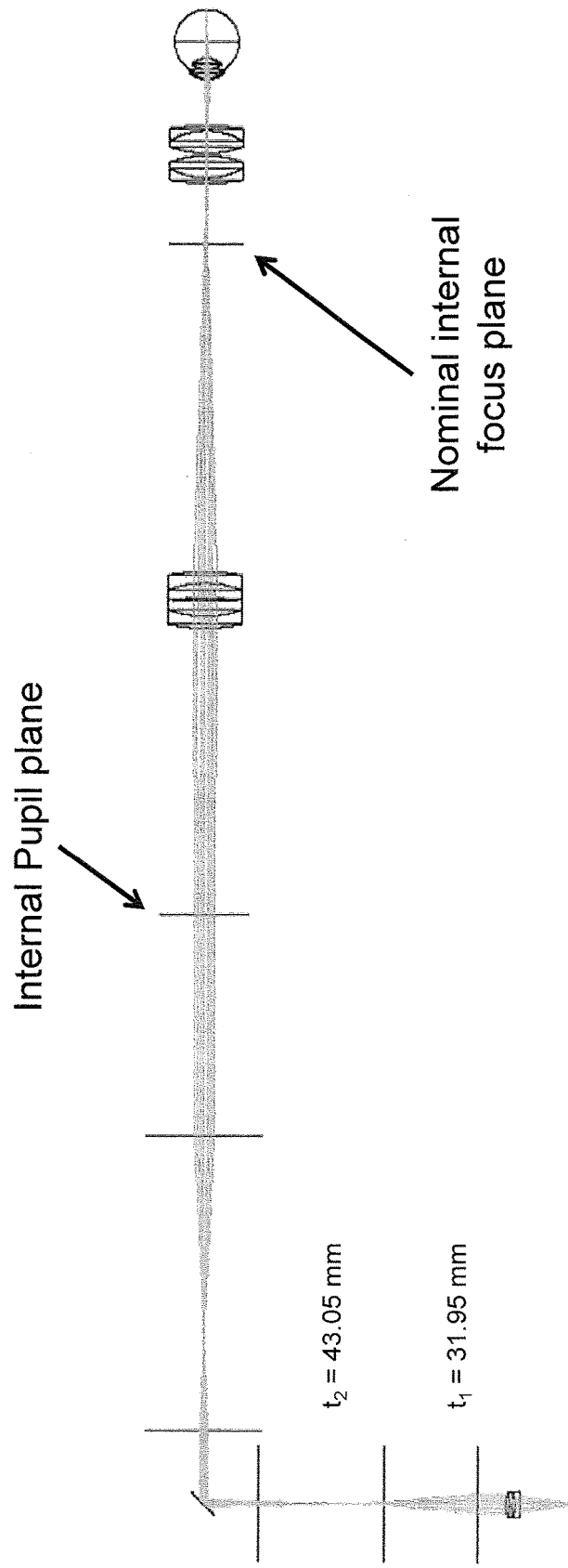
Figure 7E:
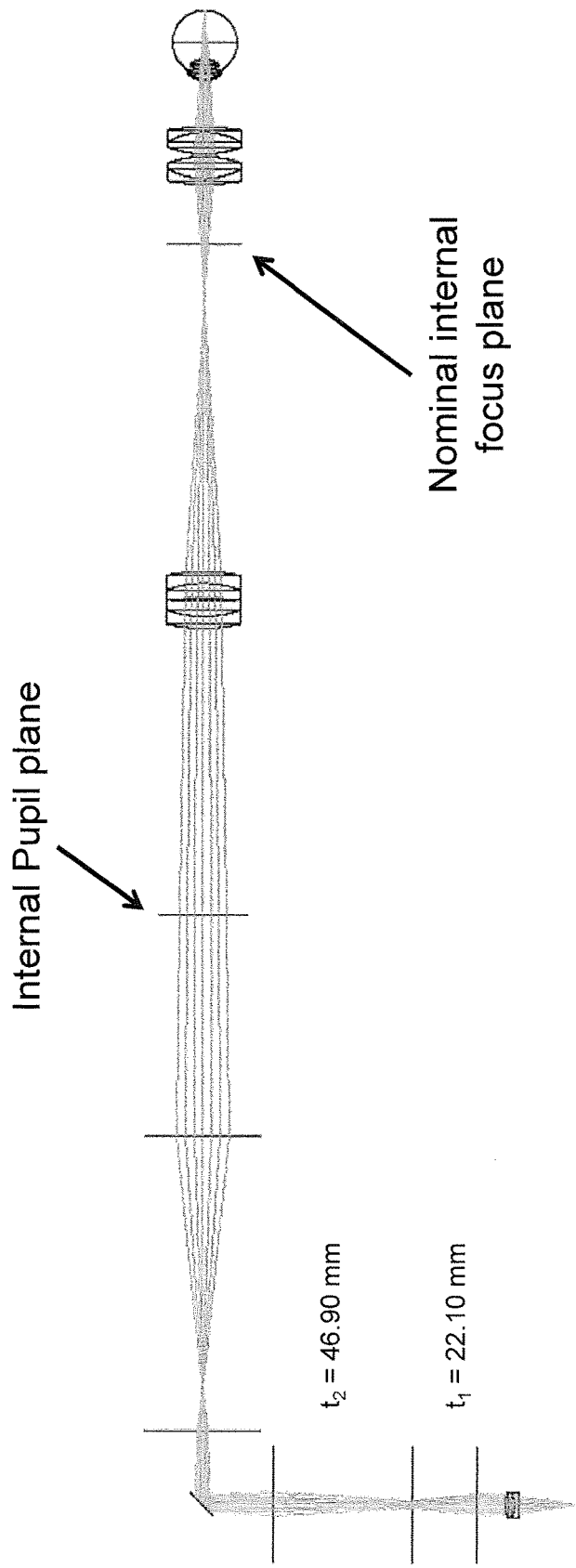
Figure 7F:
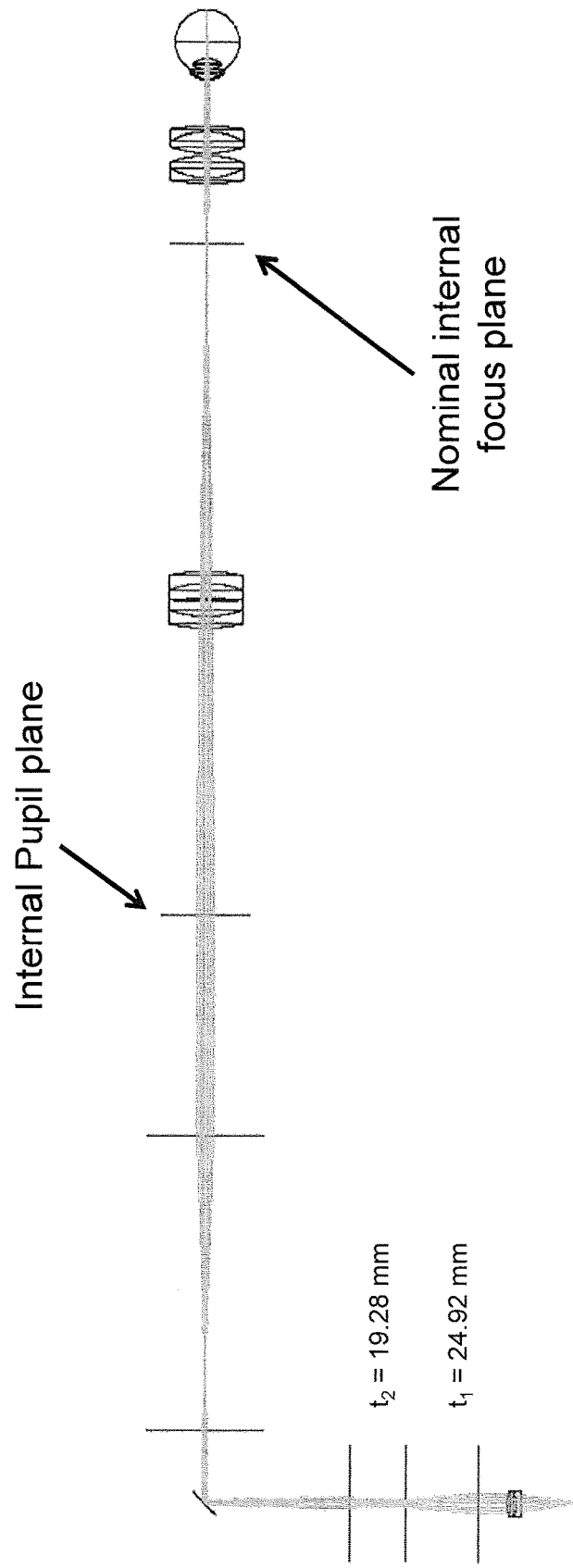

As illustrated in FIG. 7B, the system NA may be reduced for minimum beam size by changing the lens spacings to t1=24.70 and t2=2.00 mm. As illustrated in FIG. 7C, the focus is adjusted to accommodate −30 D of myopia by changing lens spacings to t1=38.70 mm and t2=24.60 mm at maximum numerical aperture and beam diameter. As illustrated in FIG. 7D, the same system is adjusted to t1=31.95 and t2=43.05 for minimum numerical aperture and beam diameter. In FIG. 7E, the focus is adjusted to accommodate +30 D of hyperopia by changing lens spacings to t1=22.10 mm and t2=46.90 mm at maximum numerical aperture and beam diameter. Finally, in FIG. 7F, the same system is adjusted to t1=24.92 and t2=19.28 for minimum numerical aperture and beam diameter.

Figure 7G:
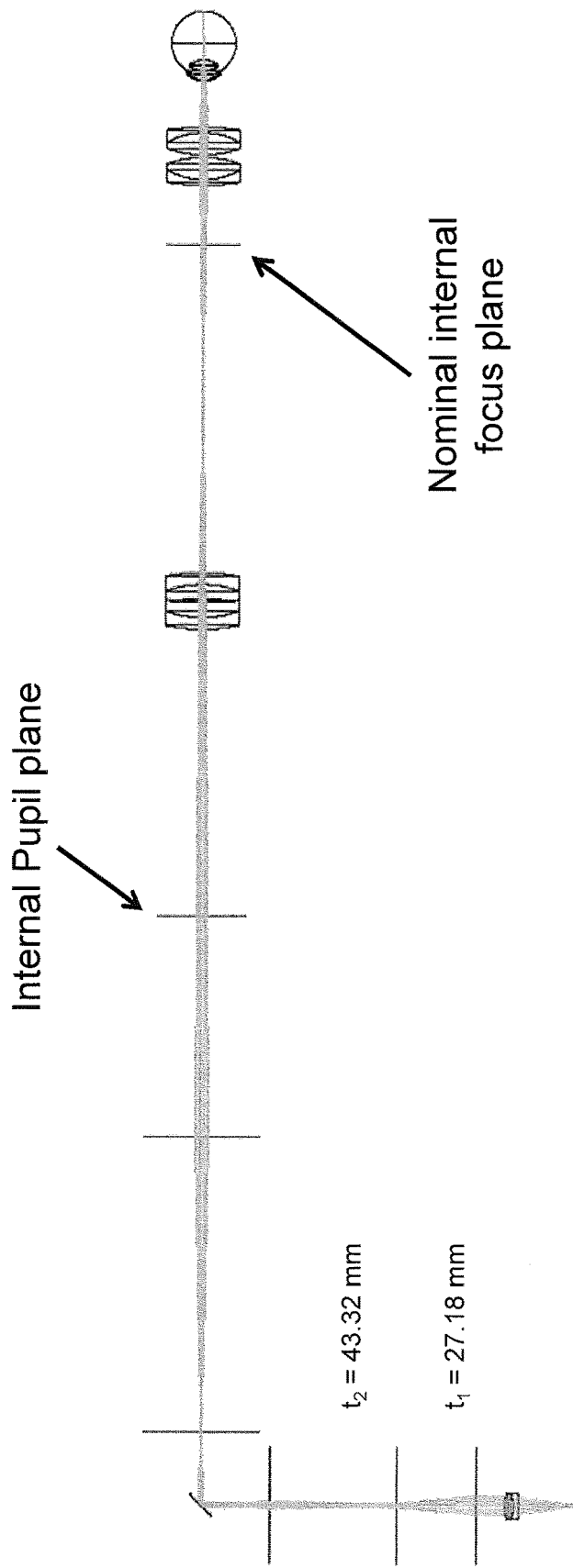

Referring now to FIG. 7G, a diagram of an example implementation of a retinal imaging system using a HT with 3× relay beam expander, with an extended focal range to +60 D to −30 D to accommodate a full range from myopia to aphakic hyperopia is illustrated. As used herein, "aphakic hyperopia" refers to clinical condition of severe farsightedness in a patient missing a natural or replacement intraocular lens. As illustrated in FIG. 7G, the HT lens powers and separations t1=27.18 mm and t2=43.32 mm are defined for one low magnification embodiment.

Figure 8A:
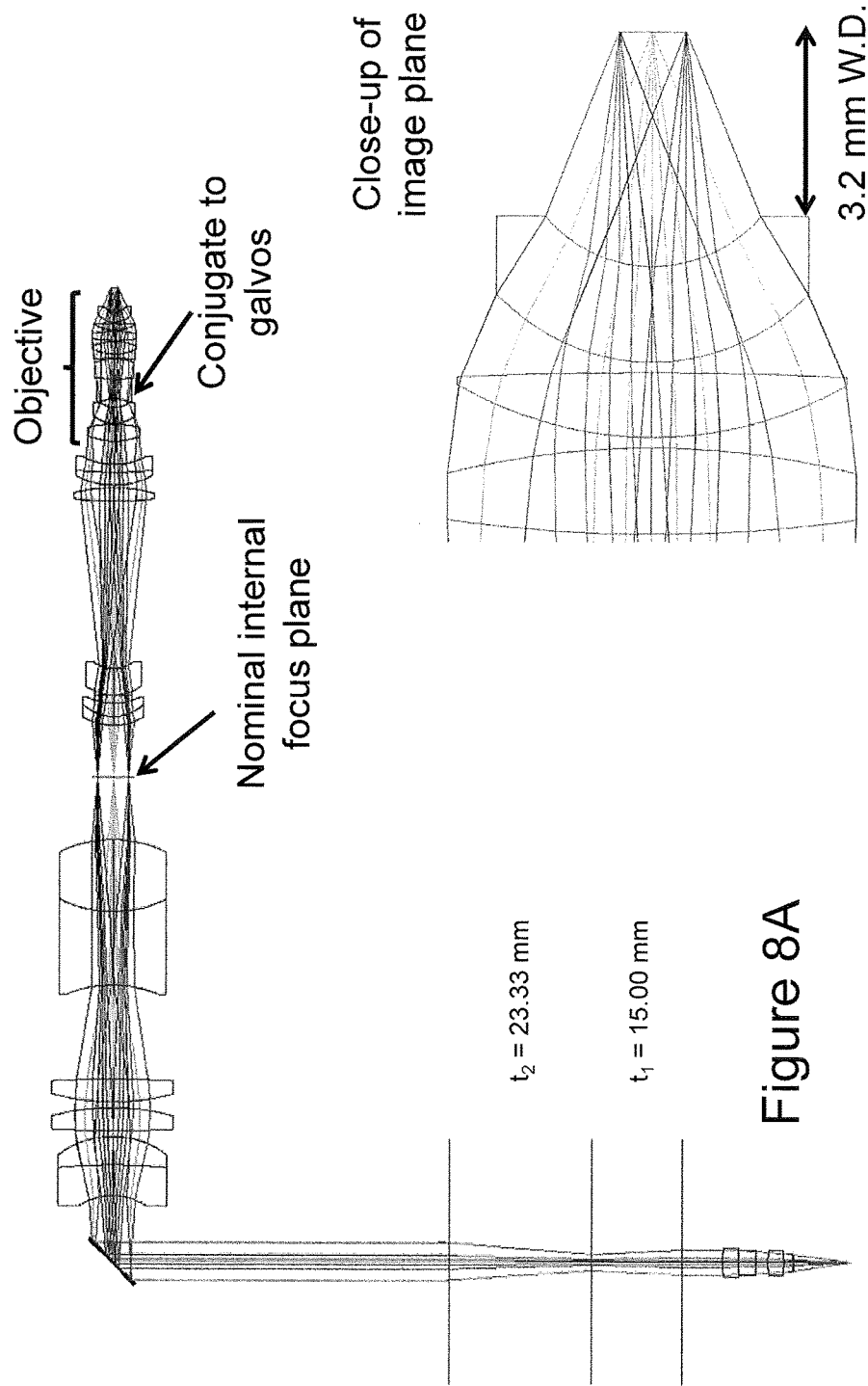
FIGS. 8A through 8B are diagrams illustrating an imaging system suitable for imaging the cornea including a hybrid telescope in accordance with some embodiments of the present inventive concept.
Figure 8B:
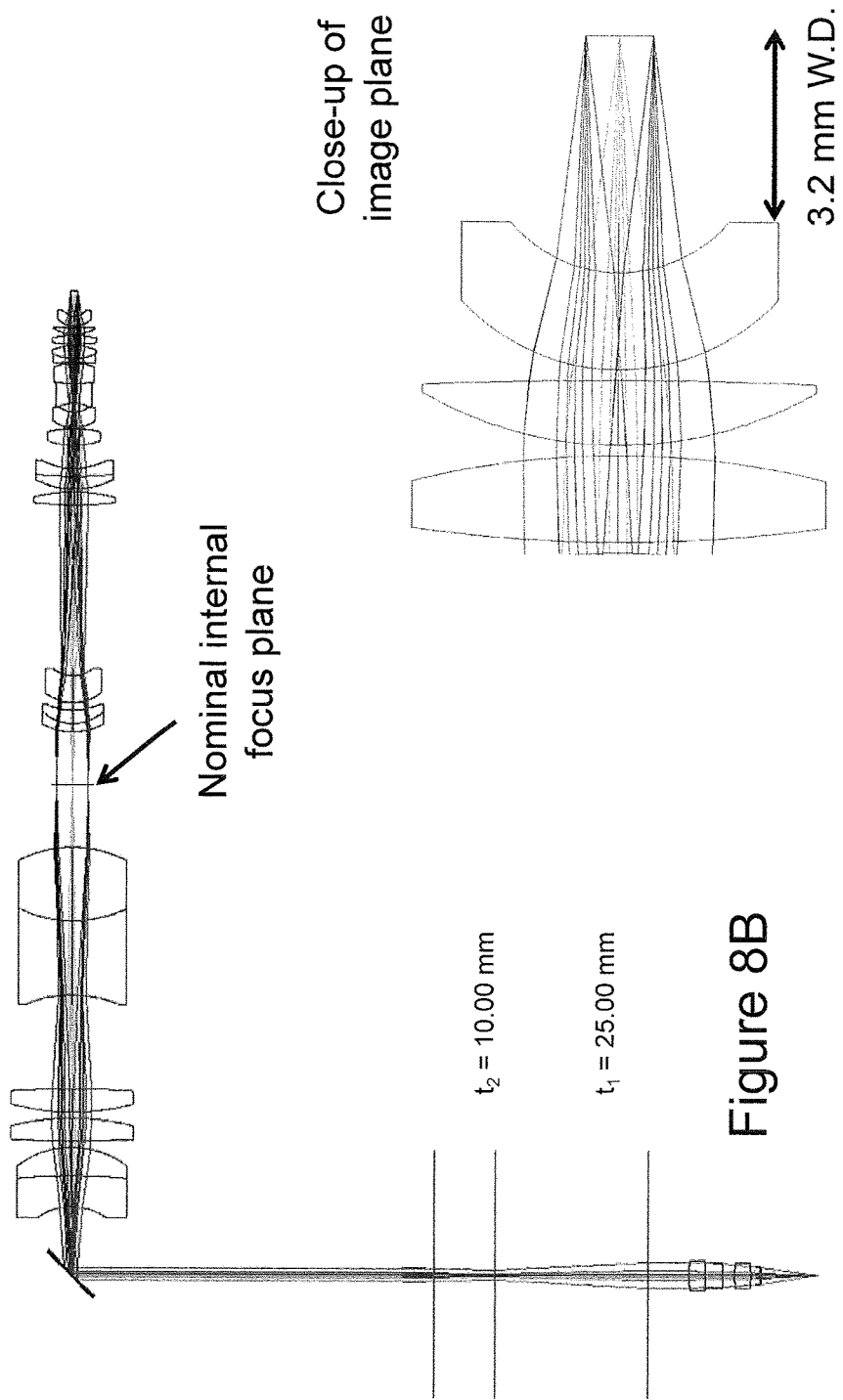

Referring to FIGS. 8A and 8B, diagrams illustrating example implementations of a scanning microscope imaging system suitable to high resolution cornea imaging will be discussed. In embodiments illustrated in FIGS. 8A and 8B, the system has an effective f-number range of 1.4 to 4 and a zoom range of approximately 3×, providing imaging attributes suitable for the cellular imaging of a corneal confocal microscope at the high numerical aperture (NA) end of the range and full thickness cornea image at the low NA end of the range.

As illustrated in FIGS. 8A-8B, the cornea imaging system includes an infinity corrected microscope objective at 3.2 mm working distance, an approximate 3× zoom (numerical aperture or beam diameter range), and field of view of 1.2 mm. At f/1.4, the beam has a diffraction limited diameter of 1.4 µm and a depth of field of 14 µm. At f/4, the beam has a diffraction limited diameter of 4.2 µm and a depth of field of 124 µm. The ability to switch between these modes of imaging offers a significant clinical advantage in providing a single tool for cellular level imaging and tomographic imaging. This configuration can fold into the infinity space of a stereo zoom microscope for simultaneous full field visual and video imagery, coincident with the multi-range scanning optical imagery. Although certain configurations have been discussed herein as example, it will be understood that embodiments of the present inventive concept are not limited to these configurations. Alternative configurations will be apparent to those skilled in the art to meet specific design objectives.

Figure 9A:
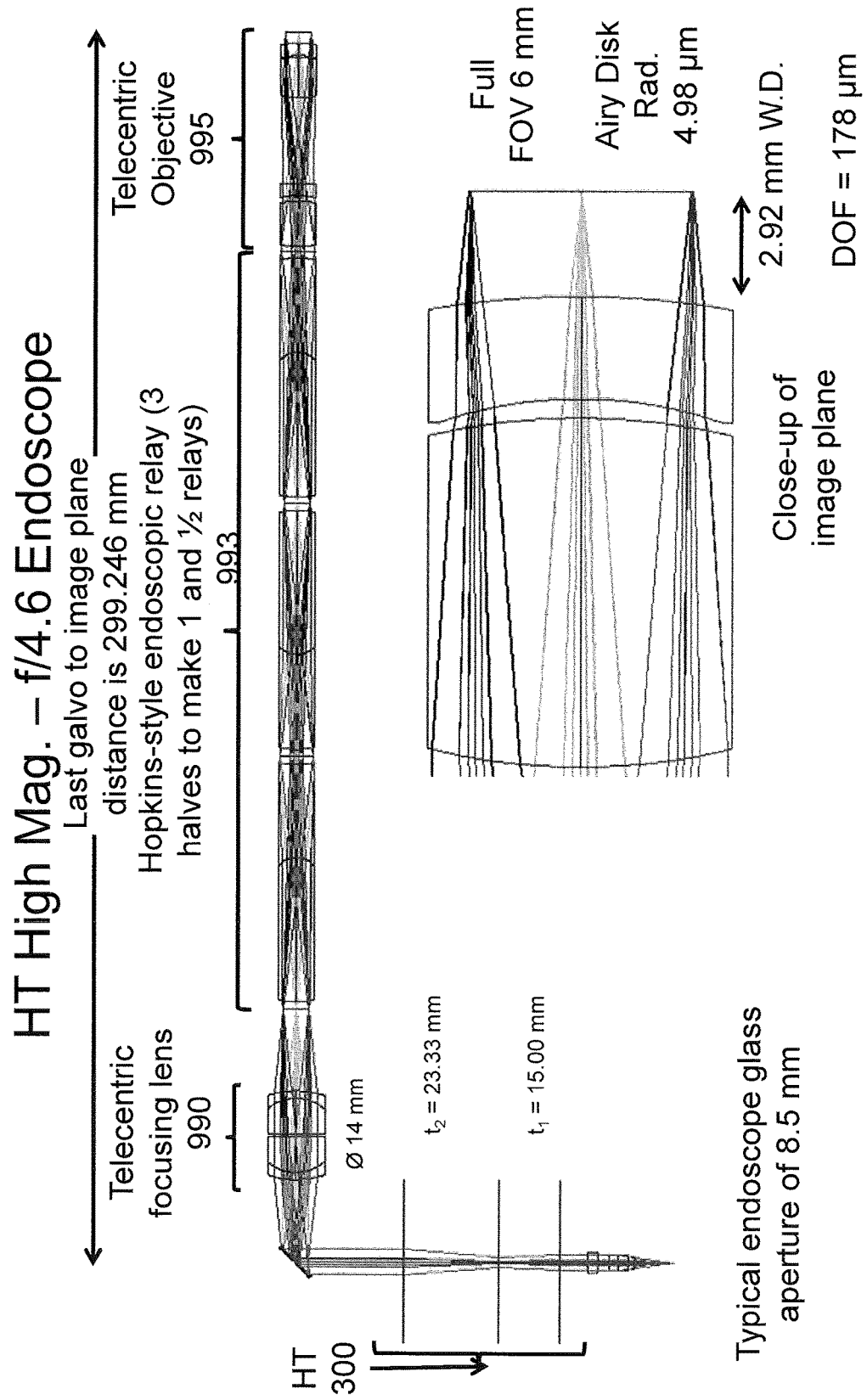
FIGS. 9A through 9C are diagrams illustrating an endoscope imaging system including a hybrid telescope in accordance with some embodiments of the present inventive concept.
Figure 9B:
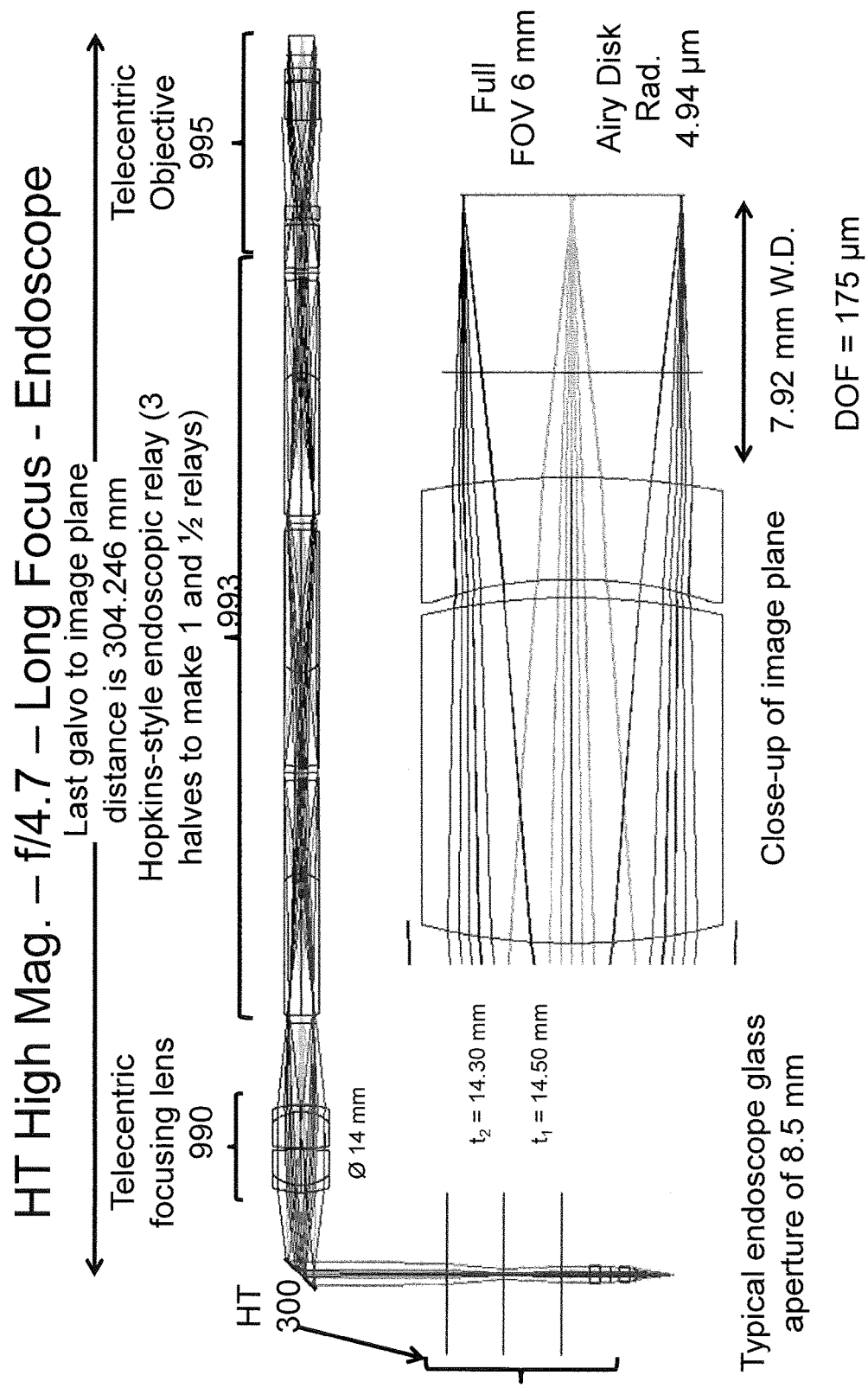
Figure 9C:
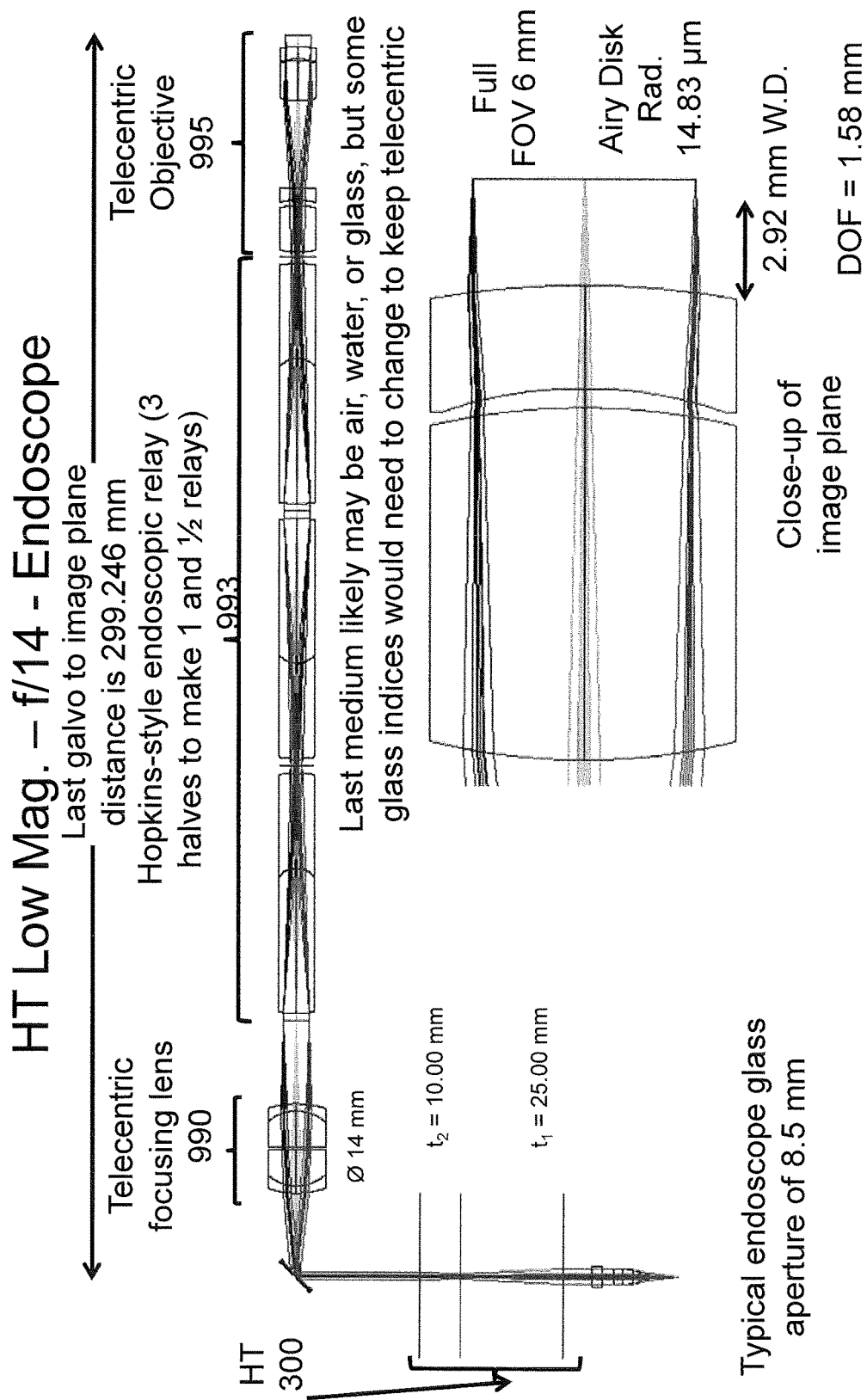

Referring now to FIGS. 9A through 9C, diagrams illustrating an example implementation of an endoscope imaging system using a HT in accordance with embodiments of the present inventive concept will be discussed. As illustrated in the figures, the endoscope configuration comprises a HT 300, followed by a telecentric mirror relay (telecentric focusing lens) 990, and a Hopkins-style endoscope relay 993 followed by a final telecentric objective 995, offering a 30 cm long scanning beam rigid endoscope with variable NA and focal length.

As illustrated in FIG. 9A, the HT 300 (t1=15.00 mm and t2=23.33 mm) is configured for f/4.6 operation, with a 3 mm working distance (effective focal length), a depth of field (DOF) of 178 µm, a beam resolution of 5 µm, and a field of view (FOV) of 6 mm. In FIG. 9B, the HT settings (t1=14.5 mm and t2=14.30 mm) are modified for a longer working distance of 8 mm, maintaining f/4.7 operation with 175 µm depth of field, 5 µm beam resolution and 6 mm field of view. In FIG. 9C, (t1=25.00 mm and t2=10.00 mm) the close 3 mm working distance is preserved, the NA is reduced to f/14 for a beam resolution of 15 µm and a depth of field of 1.58 mm. The HT lens powers and separations t1 and t2 are also illustrated on the respective figures.

Figure 10:
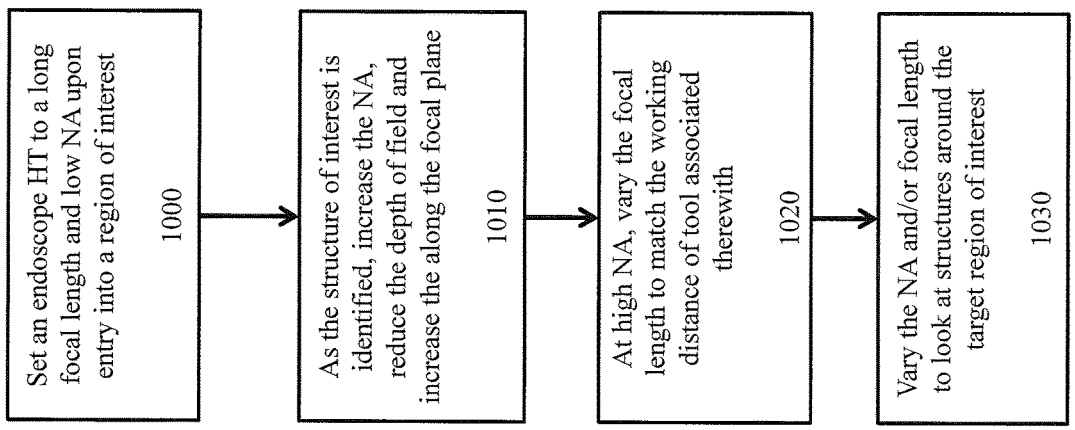
FIG. 10 is a flowchart illustrating example operations of a system utilizing an HT in accordance with some embodiments of the present inventive concept.

Referring now to FIG. 10, an exemplary method of utilizing a variable focus and zoom of a scanning beam telescope in accordance with some embodiments of the present inventive concept will be discussed. Operations begin at block 1000 by setting an endoscope HT to a long focal length and low NA upon entry into a region of interest to maximize the initial imaging range of the system.

As a structure of interest is identified, the NA is increased; reducing the depth of field but increasing the brightness along the focal plane (block 1010). At high NA, the focal length is varied to allow the endoscope to be used with tools, such as biopsy forceps, such that the focal length matches the working distance of, for example, the forceps or the like (block 1020). The numerical aperture and the focal length may be changed as desired to look at structures around the target region of interest (block 1030). As discussed above, some embodiments of the present inventive concept are used in conjunction with an OCT system. In an OCT system, as the focal length or NA of the HT is varied, the reference arm is coordinated to maintain the region of interest within the interferometric window. This endoscope system may be equally useful for non-interferometric scanning beam imaging systems, and for laser delivery systems.

Example embodiments are described above with reference to block diagrams and/or flowchart illustrations of systems and devices. The functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

In the drawings and specification, there have been disclosed exemplary embodiments of the inventive concept. However, many variations and modifications can be made to these embodiments without substantially departing from the principles of the present inventive concept. Accordingly, although specific terms are used, they are used in a generic and descriptive sense only and not for purposes of limitation, the scope of the inventive concept being defined by the following claims.

What is claimed is:

1. An optical coherence tomography (OCT) imaging system comprising:
 a source of broadband optical radiation coupled to a sample arm of the OCT imaging system;
 a beam shaping optical assembly in the sample arm of the OCT imaging system, the beam shaping optical assembly being configured to receive optical radiation from the source as a beam of optical radiation and to shape a spatial profile of the beam of optical radiation;
 a scan mirror assembly coupled to the beam shaping optical assembly in the sample arm of the OCT system;
 wherein the beam shaping optical assembly comprises a lens assembly configured to:
  change a numerical aperture (NA) of the OCT system without changing a focus of the OCT system;
  to change a focus of the OCT system without changing a NA of the system; or
  to change both the NA and the focus of the OCT system responsive to a control input; and
 an objective lens assembly coupled to the beam shaping optical assembly.

2. The OCT imaging system of claim 1, wherein the beam shaping optical assembly comprises a hybrid telescope (HT), the HT comprising:
 a first positive lens following a collimator;
 a second, movable, negative lens following the first positive lens; and a third, moveable, positive lens following the second, movable, negative lens and preceding the scan mirror assembly.

3. The OCT imaging system of claim 2, further comprising a controller configured to move lenses within the beam shaping optical assembly lenses in response to a command to adjust the NA or focus.

4. The OCT imaging system of claim 3, wherein the controller comprises one of a piezo translator and a stepper motor.

5. The OCT imaging system of claim 3, wherein the controller is controlled by a user external to the system.

6. The OCT system of claim 2, further comprising:
an objective lens assembly for imaging an eye;
wherein the system including the beam shaping optical assembly, the objective lens assembly and any additional optical elements between the beam shaping optical assembly and the objective lens assembly has a total focal power range of 60 Diopters (D) and operates between +30 to −30 D and wherein the numerical aperture is adjustable over at least a factor of 2; and
wherein the system is configured to deliver optical beam diameters at a cornea between about 2 mm to about 6 mm.

7. The OCT system of claim 2, wherein the system is adjustable to operate with a total focal power between +60 to −30 D.

8. The OCT system of claim 2, wherein the objective lens assembly comprises an objective lens set following the scan mirror assembly, wherein the HT provides a range of focusing powers between +40 to −20 D and wherein the objective lens set provides an additional focusing range of +20 to −10 D.

9. The OCT system of claim 2, further comprising a beam expander following the scan mirror assembly.

10. The OCT system of claim 9, wherein dimensions of mirrors in the scan mirror assembly are from about 3 mm to about 6 mm.

11. The OCT system of claim 2, wherein the objective lens assembly comprises an objective lens set that does not require focusing.

12. A controller for an optical coherence tomography (OCT) imaging system, the imaging system comprising a collimator in a sample arm of the OCT imaging system configured to receive an optical fiber couple to a source of the OCT imaging system, a scan mirror assembly coupled to the collimator in the sample arm of the OCT imaging system a hybrid telescope preceding the scan mirror assembly in the sample arm of the OCT imaging system between the collimator and the scan mirror assembly, the controller comprising:
a means for controlling two or more lenses of the hybrid telescope, wherein the hybrid telescope comprises:
a first positive lens following the collimator;
a second, movable, negative lens following the first positive lens; and
a third, moveable, positive lens following the second movable, negative lens and preceding the scan mirror assembly,
wherein the means for controlling comprises means for controlling the second, movable, negative lens, the third moveable, positive lens or both to change a numerical aperture (NA) of the system, a focus of the system or both the NA and the focus responsive to a control input of the controller.

* * * * *